United States Patent
Filiano et al.

(10) Patent No.: US 11,679,104 B2
(45) Date of Patent: Jun. 20, 2023

(54) COMPOSITIONS AND METHODS OF ENHANCING THE HOMING AND/OR ENGRAFTMENT OF HEMATOPOIETIC CELLS IN THE CENTRAL NERVOUS SYSTEM

(71) Applicants: Duke University, Durham, NC (US); University of Virginia Patent Foundation, Charlottesville, VA (US)

(72) Inventors: Anthony Filiano, Durham, NC (US); Joanne Kurtzberg, Durham, NC (US); Jonathan Kipnis, Charlottesville, VA (US)

(73) Assignees: Duke University, Durham, NC (US); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/772,726

(22) PCT Filed: Dec. 15, 2018

(86) PCT No.: PCT/US2018/065889
§ 371 (c)(1),
(2) Date: Jun. 12, 2020

(87) PCT Pub. No.: WO2019/118951
PCT Pub. Date: Jun. 20, 2019

(65) Prior Publication Data
US 2020/0316039 A1    Oct. 8, 2020

Related U.S. Application Data

(60) Provisional application No. 62/665,773, filed on May 2, 2018, provisional application No. 62/646,996, filed on Mar. 23, 2018, provisional application No. 62/640,110, filed on Mar. 8, 2018, provisional application No. 62/599,207, filed on Dec. 15, 2017.

(51) Int. Cl.
*A61P 25/28* (2006.01)
*A61K 31/444* (2006.01)

(52) U.S. Cl.
CPC ............ *A61K 31/444* (2013.01); *A61P 25/28* (2018.01)

(58) Field of Classification Search
CPC ...................................................... A61P 25/28
See application file for complete search history.

(56) References Cited

U.S. PATENT DOCUMENTS

| | | |
|---|---|---|
| 2017/0080031 A1 | 3/2017 | Li et al. |
| 2017/0119899 A1 | 5/2017 | Kannan et al. |
| 2017/0327844 A1 | 11/2017 | Pan |

OTHER PUBLICATIONS

Capotondo, A., et al. "Brain conditioning is instrumental for successful microglia reconstitution following hematopoietic stem cell transplantation." PNAS. (Sep. 11, 2012), vol. 109, No. 37, pp. 15018-15023. (Year: 2012).*
Capotondo et al., "Brain conditioning is instrumental for successful microglia reconstitution following hematopoietic stem cell transplantation", PNAS, 2012, 109(37), 15018-15023.
Han et al., "An updated assessment of microglia depletion: current concepts and future directions", Molecular Brain, 2017, 10(25), 1-8.
Elmore et al., "Colony-Stimulating Factor 1 Receptor Signaling is Necessary for Microglia Viability, Unmasking a Microglia Progenitor Cell in the Adult Brain", Neuron, 2014, 82(2), 380-397.
Varvel et al., "Microglial repopulation model reveals a robust homeostatic process for replacing CNS myeloid cells", PNAS, 2012, 109(44), 18150-18155.
Ginhoux et al, "Fate Mapping Analysis Reveals that Adult Microglia Derive from Primitive Macrophages", Science, 2010, 330(6005), 841-845.
Li H., et al., "The Sequence Alignment/Map format and SAMtools," Bioinformatics, 2009, vol. 25, No. 16, pp. 2078-2079.
Li J., et al., "Conditional Deletion of the Colony Stimulating Factor—1 Receptor (C-Fms Proto-Oncogene) in Mice," Genesis, Jul. 2006, vol. 44, No. 7, pp. 328-335.
Love M I., et al., "Moderated Estimation of Fold Change and Dispersion for RNA-seq Data with DESeq2," Senome Biology, 2014, vol. 15:550, 21 pages.
Lu Z., et al., "Phagocytic Activity of Neuronal Progenitors Regulates Adult Neurogenesis," Nature Cell Biology, 2011, vol. 13, pp. 1076-1083.
Matcovitch-Natan O., et al., "Microglia Development Follows a Stepwise Program to Regulate Brain Homeostasis," Science, Aug. 19, 2016, vol. 353, No. 6301, 14 pages.
Mildner A., et al., "Microglia in the Adult Brain Arise from Ly-6chiccr2+ Monocytes Only Under Defined Host Conditions," Nature Neuroscience, Dec. 2007, vol. 10, No. 12, pp. 1544-1553.
Platt F.M., et al., "Treating Lysosomal Storage Disorders: Current Practice and Future Prospects," Biochimica et Biophysica acta, Apr. 2009, vol. 1793, No. 4, pp. 737-745.

(Continued)

*Primary Examiner* — John S Kenyon
(74) *Attorney, Agent, or Firm* — Polsinelli PC

(57) ABSTRACT

The present disclosure relates to compositions and methods for enhanced engraftment of hematopoietic cells into the brain, and to therapeutic methods of treating central nervous system (CNS) diseases and disorders in subjects where replacing CNS pot macrophages (including microglia) and other tissue-resident macrophages with donor cells would be beneficial. In particular, the present disclosure relates to the use of a microglia depleting agent to enhance engraftment of hematopoietic-derived macrophages in the brain of a subject undergoing hematopoietic cell transplantation, to treat a subject suffering from a leukodystrophy and undergoing hematopoietic cell transplantation, to treat a subject suffering from a disease mediated by microglial dysfunction and undergoing hematopoietic cell transplantation, and to related methods. The present disclosure also relates to detection within cell populations of beMcφ and microglia signatures.

9 Claims, 12 Drawing Sheets

(56) References Cited

OTHER PUBLICATIONS

Priller J., et al., "Targeting Gene-Modified Hematopoietic Cells to the Central Nervous System: Use of Green Fluorescent Protein Uncovers Microglial Engraftment," Nature Medicine, Dec. 2001, vol. 7, No. 12, pp. 1356-1361.
Prinz M., etaL, "Microglia and Brain Macrophages in the Molecular Age: From Origin to Neuropsychiatric Disease," Nature reviews. Neuroscience, May 2014, vol. 15, No. 5, pp. 300-312.
Radjavi A., et al., "Dynamics Of The Meningeal CD4(+) T-Cell Repertoire are Defined by the Cervical Lymph Nodes and Facilitate Cognitive Task Performance in Mice," Molecular Psychiatry, May 2014, vol. 19, No. 19, pp. 531-533.
Ritchie M E., et al., "Limma Powers Differential Expression Analyses for RNA-Sequencing and Microarray Studies," Nucleic Acids Research, 2015, vol. 43(7), 13 pages.
Rolls A., et al., "Two Faces of Chondroitin Sulfate Proteoglycan in Spinal Cord Repair: A Role in Microglia/Macrophage Activation," PLoS Medicine, Aug. 2008, vol. 5, No. 8, 16 pages.
Scott C.L., et al., "Bone Marrow-Derived Monocytes Give Rise to Self-Renewing and Fully Differentiated Kupffer Cells," Nature Communications, Jan. 27, 2016, vol. 7, No. 10321, 10 pages.
Shechter R., et al., "Infiltrating Blood-Derived Macrophages are Vital Cells Playing an Anti-Inflammatory Role in Recovery from Spinal Cord Injury in Mice," PLoS Medicine, Jul. 2009, vol. 6, No. 7, 17 pages.
Sheng J., et al., "Most Tissue-Resident Macrophages except Microglia are Derived from Fetal Hematopoietic Stem Cells," Immunity, Aug. 18, 2015, vol. 43, No. 2, pp. 382-393.
Silver J.D., et al., "Microarray Background Correction: Maximum Likelihood Estimation for the Normal-Exponential Convolution," Biostatistics, Apr. 2009, vol. 10, No. 2, pp. 352-363.
Srinivasan K., et al., "Untangling the Brain's Neuroinflammatory and Neurodegenerative Transcriptional Responses," Nature Communications, Apr. 21, 2016, vol. 7, No. 11295, 16 pages.
Takata K., et al., "Induced-Pluripotent-Stem-Cell-Derived Primitive Macrophages Provide a Platform for Modeling Tissue-Resident Macrophage Differentiation and Function," Immunity, Jul. 18, 2017, vol. 47, No. 1, pp. 183-198.
The Gene Ontology Consortium., "Expansion of the Gene Ontology Knowledgebase and Resources," Nucleic Acids Research, Jan. 4, 2017, vol. 45, pp. D331-D338.
Theriault P., et al., "The Dynamics of Monocytes and Microglia in Alzheimer's Disease," Alzheimers Research & Therapy, Apr. 15, 2015, vol. 7, No. 1, 10 pages.
Van De Laar L., et al., "Yolk Sac Macrophages, Fetal Liver, and Adult Monocytes Can Colonize an Empty Niche and Develop into Functional Tissue-Resident Macrophages," Immunity, Apr. 19, 2016, vol. 44, No. 4, pp. 755-768.
Walkley S.U., et al., "Bone Marrow Transplantation Corrects the Enzyme Defect in Neurons of the Central Nervous System in a Lysosomal Storage Disease," Proceedings of the National Academy of Sciences of the United States of America, Apr. 12, 1994, vol. 91, No. 8, pp. 2970-2974.
Wang Y., et al., "TREM2-Mediated Early Microglial Response Limits Diffusion and Toxicity of Amyloid Plaques," The Journal of Experimental Medicine, May 2, 2016, vol. 213, No. 5, pp. 667-675.
Wu D., et al., "Camera: A Competitive Gene Set Test Accounting for Inter-Gene Correlation," Nucleic Acids Research, Sep. 1, 2019, vol. 40, No. 17, 12 pages.
Yamasaki R., et al., "Differential Roles of Microglia and Monocytes in the Inflamed Central Nervous System," The Journal of Experimental Medicine, Jul. 27, 2014, vol. 211, No. 8, pp. 1533-1549.
Yona S., et al., "Fate Mapping Reveals Origins and Dynamics of Monocytes and Tissue Macrophages under Homeostasis," Immunity, Jan. 24, 2013, vol. 38, No. 1, pp. 79-91.
Acton S.T., et al., "Area Operators for Edge Detection," Pattern Recognition Letters, Jul. 2000, vol. 21, No. 8, pp. 771-777.
Acton S.T., et al., "Biomedical Image Analysis: Tracking Synthesis Lectures On Image, Video, and Multimedia Processing," 2006, vol. 2, No. 1, pp. 1-152.

Acton S.T., "Fast Algorithms for Area Morphology," Digital Signal Processing, Jul. 2001, vol. 11, No. 3, pp. 187-203.
Ajami B., et al., "Local Self-Renewal Can Sustain CNS Microglia Maintenance and Function throughout Adult Life," Nature Neuroscience, Dec. 2007, vol. 10, No. 12, pp. 1538-1543.
Alliot F., et al., "Microglia Derive from Progenitors, Originating from the Yolk Sac, and Which Proliferate in the Brain," Brain Research Developmental Brain Research, Nov. 18, 1999, vol. 117, No. 2, pp. 145-152.
Anders S., et al., "HTSeqa Python Framework to Work with High-Throughput Sequencing Data," Bioinformatics, 2015, vol. 31, pp. 166-169.
Andrews S., et al., "FastQC: A Quality Control Tool for High Throughput Sequence Data," Babraham Bioinformatics, 2010, 6 pages.
Ashburner M., et al., "Gene Ontology: Tool for the Unification of Biology," Nature Genetics, 2000, vol. 25, pp. 25-29.
Beattie L., et al., "Bone Marrow-Derived and Resident Liver Macrophages Display Unique Transcriptomic Signatures But Similar Biological Functions," Journal of Hepatology, Oct. 2016, vol. 65, No. 4, pp. 758-768.
Bolger A.M., et al., "Trimmomatic: A Flexible Trimmer for Illumina Sequence Data," Bioinformatics, Aug. 1, 2014, vol. 30, No. 15, pp. 2114-2120.
Bosco N., et al., "Auto-Reconstitution of the T-Cell Compartment by Radioresistant Hematopoietic Cells Following Lethal Irradiation and Bone Marrow Transplantation," Experimental Hematology, Mar. 2010, vol. 38, No. 3, pp. 222-232.
Bruttger J., et al., "Genetic Cell Ablation Reveals Clusters of Local Self-Renewing Microglia in the Mammalian Central Nervous System," Immunity, Jul. 21, 2015, vol. 43, No. 1, pp. 92-106.
Butovsky O., et al., "Selective Ablation of Bone Marrow-Derived Dendritic Cells Increases Amyloid Plaques in a Mouse Alzheimer's Disease Model," The European Journal of Neuroscience, Jul. 2007, vol. 26, No. 2, pp. 413-416.
Butovsky O., et al., "Glatiramer Acetate Fights Against Alzheimer's Disease by Inducing Dendritic-Like Microglia Expressing Insulin-Like Growth Factor 1," Proceedings of the National Academy of Sciences of the United States of America, Aug. 1, 2006, vol. 103, No. 31, p. 11784-11789.
Butovsky O., et al., "Modulating Inflammatory Monocytes with a Unique Microrna Gene Signature Ameliorates Murine ALS," The Journal of Clinical Investigation,Sep. 2012, vol. 122, No. 9, pp. 3063-3087.
Carvalho B.S., et al., "A Framework for Oligonucleotide Microarray Preprocessing," Bioinformatics, Oct. 1, 2010, vol. 26, No. 19, pp. 2363-2367.
Chen S.K., et al., "Hematopoietic Origin of Pathological Grooming in Hoxb8 Mutant Mice," Cell, May 28, 2010, vol. 141, No. 5, pp. 775-785.
Chiu I.M., et al., "A Neurodegeneration-Specific Gene-Expression Signature of Acutely Isolated Microglia from an Amyotrophic Lateral Sclerosis Mouse Model," Cell Reports, Jul. 25, 2013, vol. 4, No. 2, pp. 385-401.
Conway J.R., et al., "UpSetR: A More Scalable Alternative to Venn and Euler Diagrams for Visualizing Intersecting Sets," Bioinformatics, Sep. 15, 2017, vol. 33, No. 18, pp. 2938-2940.
Cronk J.C., et al., "Methyl-CpG Binding Protein 2 Regulates Microglia and Macrophage Gene Expression in Response to Inflammatory Stimuli," Immunity, Apr. 21, 2015, vol. 42, No. 4, pp. 679-691.
Davalos D., et al., "ATP Mediates Rapid Microglial Response to Local Brain Injury in Vivo," Nature Neuroscience, Jun. 2005, vol. 8, No. 6, pp. 752-758.
Derecki N.C., et al., "Wild-Type Microglia Arrest Pathology in a Mouse Model of Rett Syndrome," Nature, Mar. 18, 2012, vol. 484, No. 7392, pp. 105-109.
Dobin A., et al., "STAR: Ultrafast Universal RNA-Seq Aligner," Bioinformatics, Jan. 1, 2013, vol. 29, No. 1, pp. 15-21.
Epelman S., et al., "Embryonic and Adult-Derived Resident Cardiac Macrophages are Maintained through Distinct Mechanisms at Steady State and During Inflammation," Immunity, Jan. 16, 2014, vol. 40, No. 1, pp. 91-104.

(56) References Cited

OTHER PUBLICATIONS

Filiano A.J., et al., "Unexpected Role of Interferon-Gamma in Regulating Neuronal Connectivity and Social Behaviour," Nature, 2016, vol. 535, pp. 425-429.
Gautier L., et al., "Affy—Analysis of Affymetrix Genechip Data at the Probe Level," Bioinformatics, 2004, vol. 20, No. 3, pp. 307-315.
Gibbings S.L., et al., "Transcriptome Analysis Highlights the Conserved Difference between Embryonic and Postnatal-Derived Alveolar Macrophages," Blood, Sep. 10, 2015, vol. 126, No. 11, pp. 1357-1366.
Ginhoux F., et al., "Microglia Arise from Extra-Embryonic Yolk Sac Primitive Progenitors," Medecine Science (Paris), 2011, vol. 27, No. 8-9, pp. 719-724.
Goldmann T., et al., "A New Type of Microglia Gene Targeting Shows TAK1 to be Pivotal in CNS Autoimmune Inflammation," Nature Neuroscience, Nov. 2013, vol. 16, No. 11, pp. 1618-1626.
Hanzelmann S., et al., "GSVA: Gene Set Variation Analysis for Microarray and RNA-Seq Data," BMC bioinformatics, Jan. 16, 2013, vol. 14, No. 7, 15 pages.
Harrow J., et al., "GENCODE: The Reference Human Genome Annotation for the ENCODE Project," Genome Research, Sep. 2012, vol. 22, No. 9, pp. 1760-1774.
Heng T.S, et al., "The Immunological Genome Project: Networks of Gene Expression in Immune Cells," Nature Immunology, Oct. 2008, vol. 9, No. 10, pp. 1091-1094.
Hoeffel G., et al., "C-Myb(+) Erythro-Myeloid Progenitor-Derived Fetal Monocytes Give Rise to Adult Tissue-Resident Macrophages," Immunity, Apr. 21, 2015, vol. 42, No. 4, pp. 665-678.
Hsiao E.Y., et al., "Modeling an Autism Risk Factor in Mice Leads to Permanent Immune Dysregulation," Proceedings of the National Academy of Sciences of the United States of America, Jul. 31, 2012, vol. 109, No. 31, p. 12776-12781.
Huang Y., et al., "Repopulated Microglia are Solely Derived from the Proliferation of Residual Microglia after Acute Depletion," Nature Neuroscience, Apr. 2018, vol. 21, No. 4, pp. 530-540.
International Preliminary Report on Patentability for the Application No. PCT/US2018/065889, dated Jun. 25, 2020, 15 pages.
International Search Report and Written Opinion for PCT/US2018/065889, dated Apr. 19, 2019, 20 Pages.
Irizarry R.A., et al., "Summaries of Affymetrix Genechip Probe Level Data," Nucleic acids Research, Feb. 15, 2003, vol. 31, No. 4, 8 pages.
Jay T.R., et al., "TREM2 Deficiency Eliminates TREM2+ Inflammatory Macrophages and Ameliorates Pathology In Alzheimer's Disease Mouse Models," The Journal of Experimental Medicine, Mar. 9, 2015, vol. 212, No. 3, pp. 287-295.
Jung S., et al., "Non-ldentical Twins—Microglia and Monocyte-Derived Macrophages in Acute Injury and Autoimmune Inflammation," Frontiers Immunology, May 7, 2012, vol. 3, No. 89, 4 pages.
Kolde R., "Pretty Heatmaps R package version 1.0.8," Jan. 4, 2019, 2 pages.
Krivit W., et al., "Bone Marrow Transplantation as Effective Treatment of Central Nervous System Disease in Globoid Cell Leukodystrophy, Metachromatic Leukodystrophy, Adrenoleukodystrophy, Mannosidosis, Fucosidosis, Aspartylglucosaminuria, Hurler, Maroteaux-Lamy, and Sly Syndromes, and Gaucher Disease Type III," Current Opinion in Neurology, Apr. 1999, vol. 12, No. 2, 1 page.
Krivit W., et al., "Microglia: The Effector Cell for Reconstitution of the Central Nervous System Following Bone Marrow Transplantation for Lysosomal and Peroxisomal Storage Diseases," Cell Transplantation, 1995, vol. 4, No. 4, pp. 385-392.
Larochelle A., et al., "Bone Marrow-Derived Macrophages and the CNS: An Update on the Use of Experimental Chimeric Mouse Models and Bone Marrow Transplantation in Neurological Disorders," Biochimica et Biophysica acta, Mar. 2016, vol. 1862, No. 3, pp. 310-322.
Lassmann T., et al., "SAMStat: Monitoring Biases in Next Generation Sequencing Data," Bioinformatics, Jan. 1, 2011, vol. 27, No. 1, pp. 130-131.
Lavin Y., et al., "Tissue-Resident Macrophage Enhancer Landscapes are Shaped by the Local Microenvironment," Cell, Dec. 4, 2014, vol. 159, No. 6, pp. 1312-1326.
Law C.W., et al., "Voom: Precision Weights Unlock Linear Model Analysis Tools for RNA-Seq Read Counts," Genome Biology, 2014, vol. 15, No. R29, 17 pages.
Leek J.T., et al., "Capturing Heterogeneity in Gene Expression Studies by Surrogate Variable Analysis," PLoS Genetics, Sep. 2007, vol. 3, No. 9, pp. 1724-1735.
Leek J.T., et al., "The Sva Package for Removing Batch Effects and Other Unwanted Variation in High-Throughput Experiments," Bioinformatics, Mar. 15, 2012, vol. 28, No. 6, pp. 882-883.
Lex A., et al., "UpSet: Visualization of Intersecting Sets," IEEE Transactions on Visualization and Computer Graphics, Dec. 2014, vol. 20, No. 12, pp. 1983-1992.

\* cited by examiner

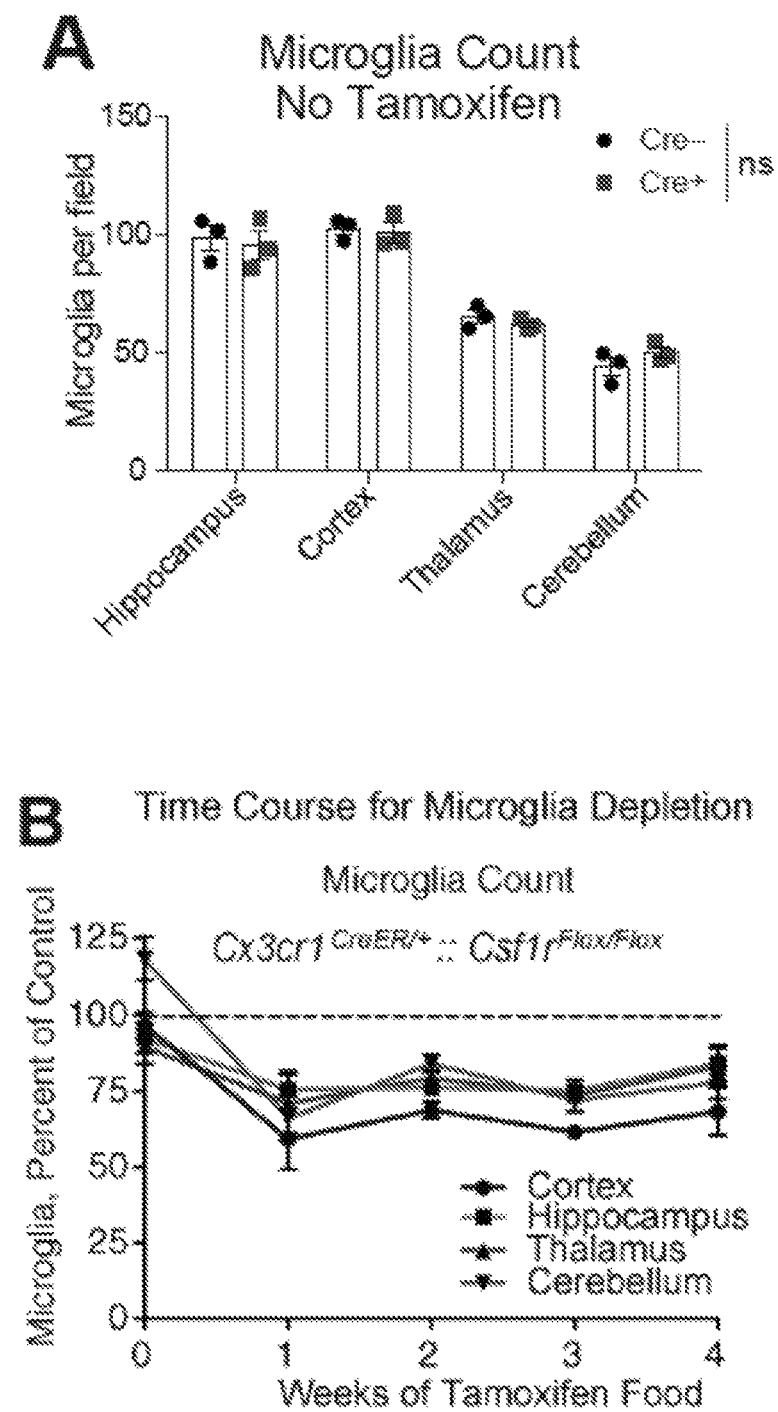
Figures 2A-B

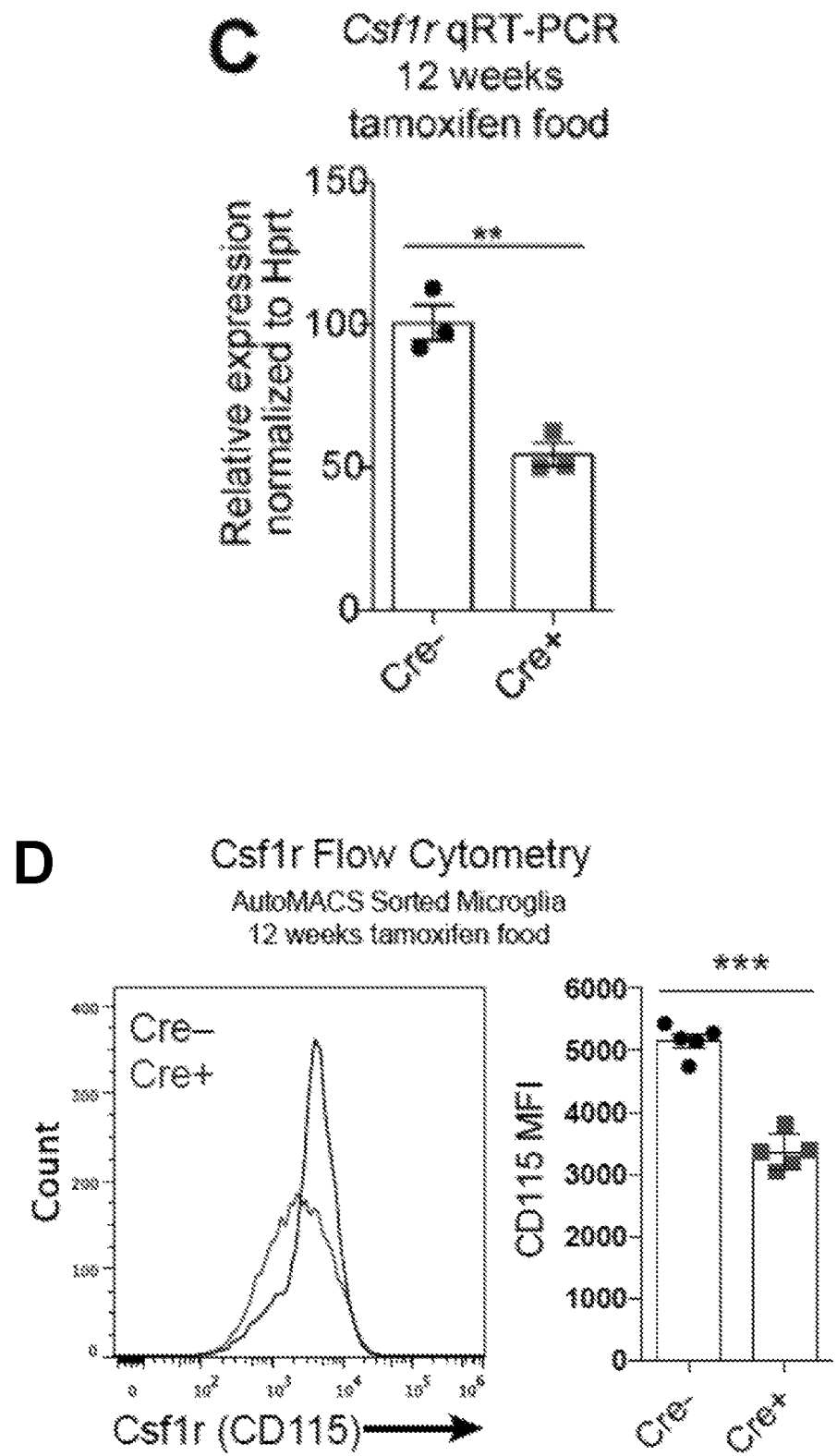
Figures 2C-D

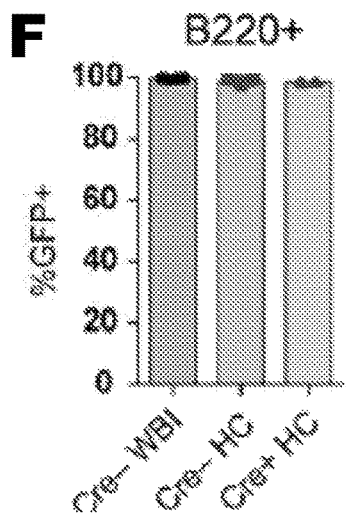
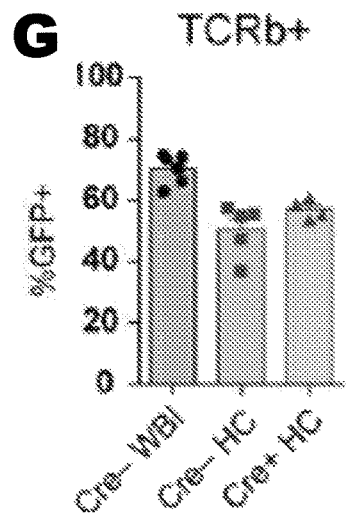
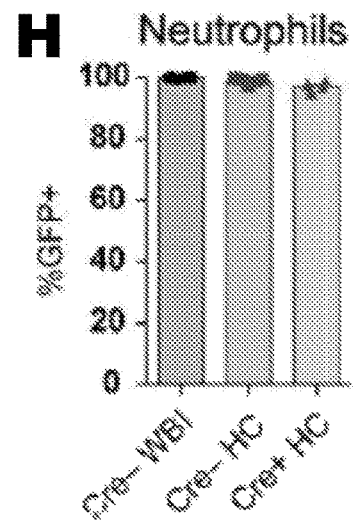
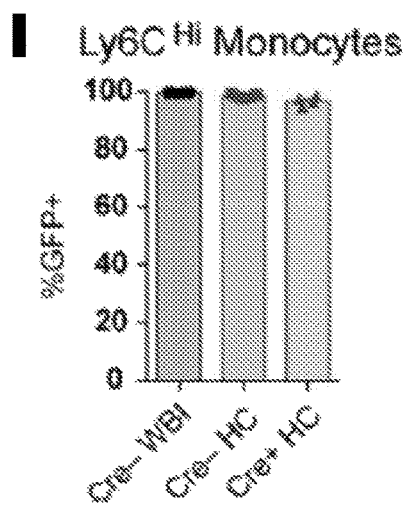
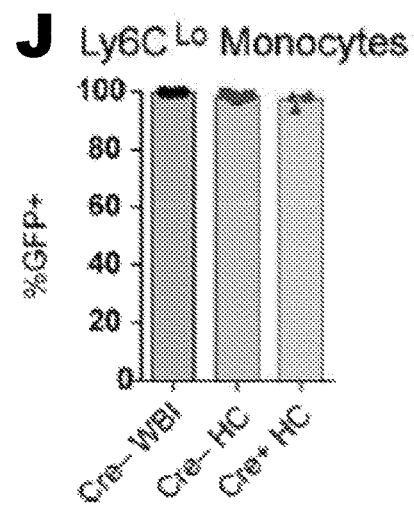
Figures 2F-J

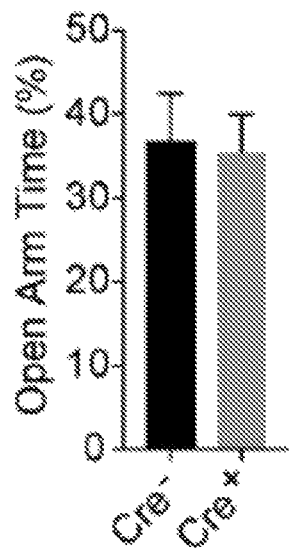
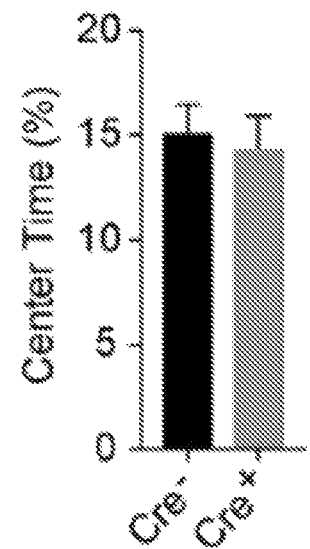
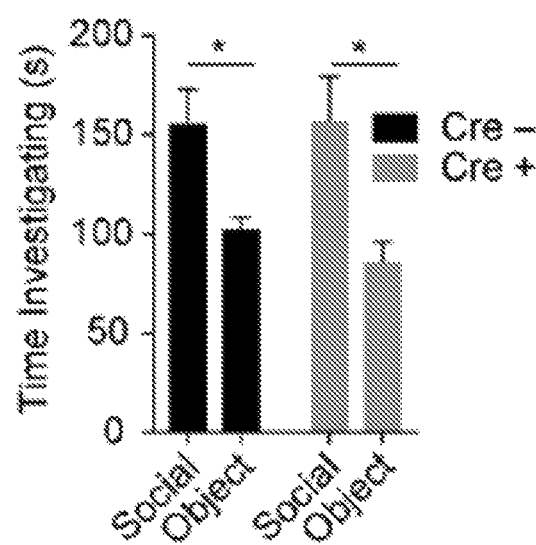
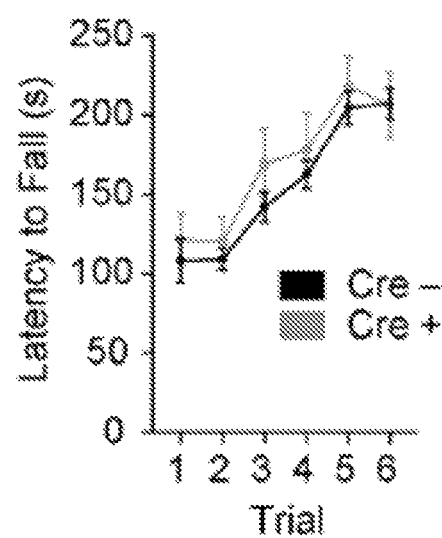
Figures 2K-N

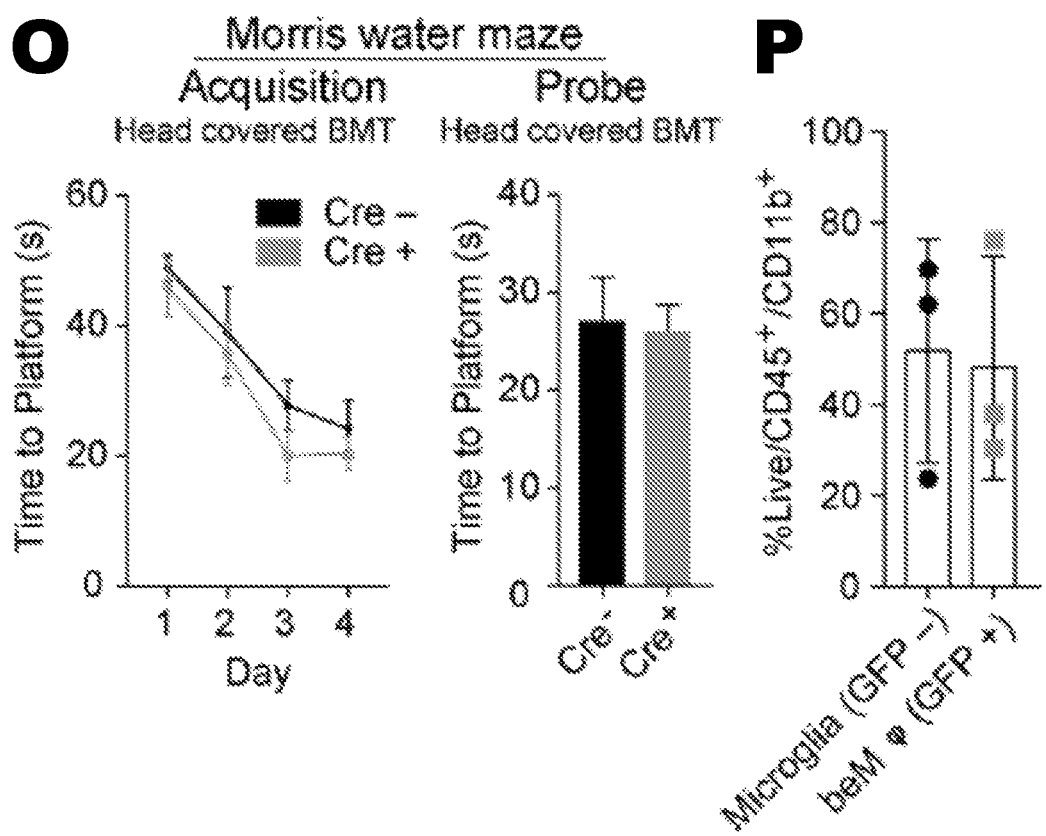
Figures 2O-P

COMPOSITIONS AND METHODS OF ENHANCING THE HOMING AND/OR ENGRAFTMENT OF HEMATOPOIETIC CELLS IN THE CENTRAL NERVOUS SYSTEM

CROSS REFERENCE TO RELATED APPLICATIONS

This application is the U.S. national phase under 35 U.S.C. § 371 of International Application No. PCT/US2018/05889, filed Dec. 15, 2018, which claims priority to U.S. Provisional Patent Application Ser. Nos. 62/599,207, filed Dec. 15, 2017, 62/640,110, filed Mar. 8, 2018, 62/646,996, filed Mar. 23, 2018, and 62/665,773, filed May 2, 2018, the contents of each of which are hereby incorporated by reference in their entirety.

BACKGROUND OF THE INVENTION

Field of the Invention

The present disclosure relates to compositions and methods for enhanced engraftment of hematopoietic cells into the brain. The present disclosure also relates to therapeutic methods of treating central nervous system (CNS) diseases and disorders in subjects where replacing CNS macrophages (including microglia) and other tissue-resident macrophages with donor cells would be beneficial, and to diagnostic methods pertaining to engrafted macrophages bearing a unique transcriptional signature.

Description of the Related Art

Dysfunctional brain macrophages (microglia) are described in many neurological disorders. Replacement of endogenous microglia can be achieved through hematopoietic cell (HC) transplantation (HCT) and is used as a vehicle for enzyme replacement and modulation of neuroinflammation in many genetic diseases affecting the brain. However, because microglia are long-lived, the efficiency of their replacement with donor cells after standard HCT is incomplete, limiting the benefits of this procedure. If more efficient and rapid engraftment could be achieved, the benefits of HCT in controlling progression of the underlying disease would be greatly enhanced. The procedure, which today is only effective in pre-symptomatic patients, could also be extended to patients with symptomatic disease. In addition, earlier and more extensive engraftment in the brain would improve outcomes in pre-symptomatic patients.

Moreover, a fundamental understanding of the nature of the engrafted cells may lead to improved therapeutic approaches to CNS diseases.

Although most tissue resident macrophage populations are initially populated by primordial yolk sac-derived macrophages (Alliot et al., 1999; Ginhoux and Merad, 2011), some are replaced with cells derived from fetal monocytes or hematopoietic stem cells (HSC), leading to either complete replacement of yolk sack-derived macrophages, or mixed populations that are dominated by cells of the fetal monocyte or HSC lineage (Epelman et al., 2014; Hoeffel et al., 2015; Sheng et al., 2015). Microglia, however, are a notable exception to this rule, and under homeostatic conditions they self-renew from the original yolk sac lineage throughout the life of the animal (Ajami et al., 2007; Bruttger et al., 2015; Elmore et al., 2014; Epelman et al., 2014; Hoeffel et al., 2015; Sheng et al., 2015).

Monocytes do not enter the healthy brain, but are seen within the brain parenchyma under certain pathological conditions, where their contribution to CNS pathology is highly debated (Butovsky et al., 2012; Chiu et al., 2013; Jay et al., 2015; Jung and Schwartz, 2012; Prinz and Priller, 2014; Theriault et al., 2015; Wang et al., 2016; Yamasaki et al., 2014). Further, the conditions required for macrophage engraftment into the CNS parenchyma are not well understood. However, hematopoietic cells readily engraft the brain after lethal whole-body irradiation and bone marrow transplantation (BMT), often assumed to be secondary to blood brain barrier (BBB) opening after irradiation (Mildner et al., 2007; Priller et al., 2001).

These peripheral-derived brain-engrafting macrophages ("beMφ") were initially noted to spatially replace microglia, tiling with resident microglia, and to develop ramifications similar to those of microglia (Mildner et al., 2007; Priller et al., 2001). These findings led to the hypothesis that hematopoietic-derived macrophages are capable of differentiating into true microglia upon engraftment. Indeed, several groups have found that the tissue environment directs macrophage differentiation, transcriptomes, and function (Beattie et al., 2016; Gibbings et al., 2015; Lavin et al., 2014; Scott et al., 2016; van de Laar et al., 2016), supporting the concept that the brain environment may be sufficient to drive differentiation of peripheral-derived microglia.

The exact nature of beMφ is not yet understood. An understanding of the conditions necessary for engraftment into the brain, and whether beMφ become true microglia, or are an independent class of resident brain macrophages that exists under defined conditions remains to be elucidated.

In the context of clinical implications, it has been shown that macrophage engraftment after BMT is beneficial in lysosomal storage disease (Krivit et al., 1999; Krivit et al., 1995; Platt and Lachmann, 2009; Walkley et al., 1994), a mouse model of obsessive-compulsive disorder (Chen et al., 2010), and some mouse models of neurodevelopmental disorders (Derecki et al., 2012; Hsiao et al., 2012). These data suggest that replacing damaged and/or deficient microglia with donor cells would benefit a host of neurological conditions.

SUMMARY OF THE INVENTION

In a first aspect, the present invention provides a method of enhancing engraftment of hematopoietic-derived macrophages in the brain of a subject undergoing hematopoietic cell (HC) transplantation (HCT), comprising administering to the subject a therapeutically effective amount of a microglia depleting agent.

In a second aspect, the present invention provides a method of treating a subject suffering from a leukodystrophy and undergoing HC transplantation comprising administering to the subject a therapeutically effective amount of a microglia depleting agent such that the homing or engraftment of the HCs are enhanced.

In a third aspect, the invention provides a method of treating a subject suffering from a disease mediated by microglial dysfunction and undergoing HC transplantation comprising administering to the subject a therapeutically effective amount of a microglia depleting agent such that the homing or engraftment of the HSCs or cord blood mononuclear cells are enhanced.

In a fourth aspect, the present invention provides a method of altering the microglial niche in the brain of a subject comprising administering to the subject a therapeutically effective amount of a microglia depleting agent and transplanting HCs.

In a fifth aspect, the present invention provides a method of engrafting hematopoietic-derived macrophages in the brain of a subject undergoing HC transplantation comprising subjecting the subject to a transplant conditioning regimen and administering a microglia depleting agent.

In a further aspect, the present invention provides a method of detecting beMφ cells in a cell population comprising analyzing the cell population for the beMφ-50 signature, wherein the presence of the beMφ-50 signature indicates that beMφ cells are present in the cell population. In a yet further aspect, the present invention provides a method of detecting microglia in a cell population comprising analyzing the cell population for the Mg-52 signature, wherein the presence of the Mg-52 signature indicates that microglia cells are present in the cell population. In a still further aspect, the present invention provides a method of differentiating between beMφ and microglia cells in a cell population comprising analyzing the genetic signature of the cell population, wherein the presence of the beMφ-50 signature indicates the presence of beMφ cells in the cell population and wherein the presence of the Mg-52 signature indicates the presence of microglia cells in the cell population.

BRIEF DESCRIPTION OF THE DRAWINGS

The accompanying drawings are included to provide a further understanding of the methods and compositions of the disclosure, and are incorporated in and constitute a part of this specification. The drawings illustrate one or more embodiment(s) of the disclosure.

DETAILED DESCRIPTION OF THE INVENTION

Figure 1A:
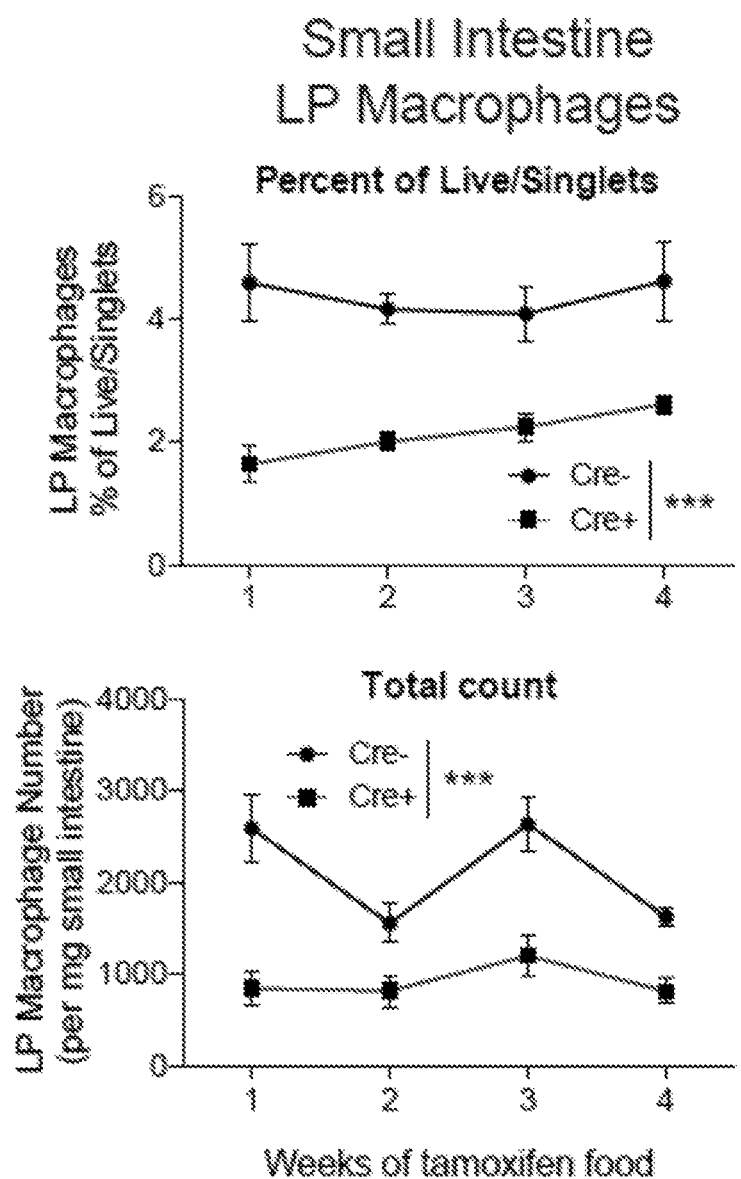
FIG. 1. Cx3cr1-expressing resident myeloid cells in the periphery are depleted in $Cx3cr1^{CreER/+}::Csf1r^{flox/flox}$ mice fed tamoxifen. (A) Counts of lamina propria macrophages (n=5-6 mice per group; Two-way ANOVA, * p<0.001; pooled from two independent experiments). (B) Counts of blood monocyte populations (n=5-6 mice per group; Two-way ANOVA, * p<0.001; ** p<0.01; * p<0.05; pooled from two independent experiments). Error bars represent±SEM.

Before the disclosed processes and materials are described, it is to be understood that the aspects described herein are not limited to specific embodiments, apparati, or configurations, and as such can, of course, vary. It is also to be understood that the terminology used herein is for the purpose of describing particular aspects only and, unless specifically defined herein, is not intended to be limiting.

It is also to be understood that unless clearly indicated otherwise by the context, embodiments disclosed for one aspect or embodiment of the invention can be used in other aspects or embodiments of the invention as well, and/or in combination with embodiments disclosed in the same or other aspects of the invention. Thus, the disclosure is intended to include, and the invention includes, such combinations, even where such combinations have not been explicitly delineated.

Definitions

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. In some embodiments, the disease comprises leukodystrophies. In other embodiments, the disease comprises diseases mediated by microglial dysfunction including, but not limited to, Rett syndrome, Autism spectrum disorder, Alzheimer's disease, frontotemporal dementia, amyotrophic lateral sclerosis, adult-onset leukoencephalopathy with axonal spheroids and pigmented glia, and other disorders where replacing central nervous system (CNS) macrophages with donor cells would be beneficial.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject is a human.

The terms "enhancing engraftment [of cells]," "the homing or engraftment is enhanced" and variations thereof are used to refer to improved speed and/or extent of engraftment of transplanted cells relative to the speed and/or extent of engraftment absent the specified circumstance or actions. In a non-limiting example, in a method of "enhancing engraftment" of certain cells in a subject comprising administering to the subject a therapeutically effective amount of a microglia depleting agent, "enhancing engraftment" refers to providing improved speed and/or extent of engraftment of the cells relative to the speed and/or extent of engraftment absent the administration of the microglia depleting agent.

As used herein, a "microglia depleting agent" is any agent capable of substantially depleting endogenous microglia in a subject. In some instances, the depletion is substantially persistent, i.e. the endogenous microglia are substantially incapable of self-renewal and repopulation. In some instances, the microglia depleting agent is selective, i.e. its effects are limited primarily to microglia and not other cell types. Unless otherwise specified, the term "microglia depleting agent" refers to one or more such agents, i.e. it may refer to a single agent, e.g. one compound, or it may refer to a combination of two or more compounds which are either independently capable of substantially depleting endogenous microglia in a subject or so function in combination.

The term "Mg-52" is used herein to refer to the gene signature of microglia as determined by the inventors and set forth herein. The term "beMφ-50" refers to the gene signature of beMφ as determined by the inventors and set forth herein.

Unless otherwise defined, all technical terms used herein have the same meaning as commonly understood by one of ordinary skill in the art to which this disclosure belongs.

Depletion of Microglia in the Brain and Related Methods

The inventors have discovered that microglia depleting agents can accelerate and/or enhance engraftment of donor monocytes in the CNS and provide certain therapeutic benefits, and that the engrafted cells bear a unique transcriptional and functional signature. Notably, at present while the treatment of certain CNS diseases and disorders can be effected by way of hematopoietic cell transplant (i.e. subjecting a subject to a conditioning regimen and administering donor cells), and certain benefits attainted therefrom, adequate engraftment of donor cells into the brain is slow to occur, if at all. Thus, the disease progresses until adequate CNS engraftment is attained. The present invention addresses that problem, enhancing hematopoietic cell transplant in providing a mechanism for rapid and effective engraftment of donor cells in the brain.

Accordingly, in a first aspect, the present invention provides a method of enhancing engraftment of hematopoietic-derived macrophages in the brain of a subject undergoing hematopoietic cell (HC) transplantation (HCT), comprising administering to the subject a therapeutically effective amount of a microglia depleting agent.

HCT is known in the art and refers to the administration, typically intravenously, of hematopoietic cells from various donor sources, e.g. bone marrow, peripheral blood, or umbilical cord blood, and related sources such as cord blood mononuclear cells and expanded HCs. HCT as used herein also includes transplantation of manipulated cells, e.g. induced pluripotent stem cells. The transplanted cells may be autologous, allogeneic, or syngenic.

The microglia depleting agent may be administered by any technique known in the art, including local or systemic delivery. Routes of administration include, but are not limited to, oral, subcutaneous, sublingual, intracutaneous, intramuscular, intraperitoneal, intravenous, intrathecal, intracerebral, intraventricular, buccally, rectally, vaginally, ocularly, otically, or epidural injection or implantation; by inhalation, by nebulization; topical administration; transdermal; intratracheal; and intranasal administration. In certain embodiments, the microglia depleting agent is administered orally.

The microglia depleting agent may be administered as a composition comprising the agent and one or more pharmaceutically acceptable carriers, adjuvants, diluents, and/or excipients.

One of skill in the art will be able to determine suitable dosing regimens. In some embodiments, the microglia depleting agent is administered over 2 weeks. In some embodiments, the inhibitor is administered once daily. The microglia depleting agent may be administered, in a non-limiting example, at a dose within the range of 0.01 mg/kg to 500 mg/kg, or any dose within that range. As examples, the dose may include, but is not limited to, 0.1 mg/kg, 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 150 mg/kg, 200 mg/kg, 250 mg/kg, 300 mg/kg, 350 mg/kg, 400 mg/kg, or 450 mg/kg, or any other dose within the range not specifically enumerated. Similarly, the microglia depleting agent may be administered, in a non-limiting example, at any dosing range within 0.01 mg/kg to 500 mg/kg, even if not specifically enumerated, including, but not limited to 1 mg/kg to 50 mg/kg, 1 mg/kg to 100 mg/kg, 20 mg/kg to 50 mg/kg, 50 mg/kg to 100 mg/kg, 100 mg/kg to 200 mg/kg, 200 mg/kg to 300 mg/kg, 300 mg/kg to 400 mg/kg, and 400 mg/kg to 500 mg/kg.

In a second aspect, the present invention provides a method of treating a subject suffering from a leukodystrophy and undergoing HC transplantation comprising administering to the subject a therapeutically effective amount of a microglia depleting agent such that the homing or engraftment of the HCs are enhanced.

In a third aspect, the invention provides a method of treating a subject suffering from a disease mediated by microglial dysfunction and undergoing HC transplantation comprising administering to the subject a therapeutically effective amount of a microglia depleting agent such that the homing or engraftment of the HCs are enhanced.

In the second and third aspects of the invention, the enhancement in engraftment of the transplanted cells provides certain benefits, including allowing for earlier and improved disease control and possible reversal of neurological impairments. The clinical modulation of microglial activity in brain disease represents a promising therapeutic area. Engraftment with macrophages with appropriate physiological properties offers a very competitive approach in that these cells have multiple potential beneficial properties and persist in the brain for extended periods of time. The specific beneficial properties depend on the disease treated. For leukodystrophies, the transplanted cells will, for example, provide wild-type enzyme and may also help repair damage from the buildup of toxic metabolic storage products. Currently, enzyme replacement therapy is used to treat some of these diseases, but is generally not effective in ameliorating CNS disease. Transplant is effective, but the disease progresses until adequate CNS engraftment is attained. The present invention addresses that problem. In this regard, the present invention may be used in combination with gene-modified stem cell therapies that are being developed for some inherited metabolic diseases.

Leukodystrophies, which may be treated in accordance with the present invention, are known in the art and include, but are not limited to, adult-onset autosomal dominant leukodystrophy (ADLD), Aicardi-Goutieres syndrome, Alexander disease, CADASIL, Canavan disease, CARASIL, cerebrotendinous xanthomatosis, childhood ataxia and cerebral hypomyelination (CACH)/vanishing white matter disease (VWMD), Fabry disease, fucosidosis, GM1 gangliosidosis, Krabbe disease, L-2-hydroxyglutaric aciduria, megalencephalic leukoencephalopathy with subcortical cysts, metachromatic leukodystrophy, multiple sulfatase deficiency, Pelizaeus-Merzbacher disease, Pol III-Related Leukodystrophies, Refsum disease, salla disease (free sialic acid storage disease), Sjogren-Larsson syndrome, X-linked adrenoleukodystrophy, and Zellweger syndrome spectrum disorders.

The diseases mediated by microglial dysfunction which may be treated in accordance with the present invention include, but are not limited to, Rett syndrome, Autism spectrum disorder, Alzheimer's disease, frontotemporal dementia, amyotrophic lateral sclerosis, adult-onset leukoencephalopathy with axonal spheroids and pigmented glia, and other disorders where replacing central nervous system (CNS) macrophages with donor cells would be beneficial.

In some embodiments of the above aspects of the invention, the microglia depleting agent may be administered prior to the HCs. In other embodiments, the microglia depleting agent may be administered concurrently with the HCs. In still further embodiments, the microglia depleting agent may be administered after the administration of HCs.

The microglia depleting agents of the various aspects of the invention may be, in a non-limiting example, a colony stimulating factor 1 receptor (CSF1R) antagonist; CSF1R is critical for microglia survival. Non-limiting exemplary CSF1R antagonists that may be used in the present invention include PLX3397 and PLX5562.

The inventors have discovered that chronic, partial microglia depletion, resulting in a partially unfilled niche, is sufficient for beMφ to populate the niche. Accordingly, in a fourth aspect, the present invention provides a method of altering the microglial niche in the brain of a subject comprising administering to the subject a therapeutically effective amount of a microglia depleting agent and transplanting HCs.

The inventors have surprisingly found that the use of a microglia depleting agent in association with the engraftment of hematopoietic-derived macrophages in a subject, which allows for substantial repopulation of microglia by beMφ, confers certain advances and benefits over known processes and methods. The engrafted macrophages, beMφ, are transcriptionally and functionally distinct from microglia. Still, even with significant microglia replacement by beMφ, changes in overall brain function were not detected.

Accordingly, in certain embodiments of the above aspects of the invention, the engrafted cells do not alter brain function.

Also, notably, the inventors have shown that in the context of chronic microglia deficiency—without CNS irradiation, infection, or BBB compromise—circulating monocytes can engraft into the CNS and persistently fill the available niche created by depleted microglia. The fact that chronic microglia depletion (along with the inability of the remaining microglia to proliferate and repopulate the niche) is sufficient to drive beMφ engraftment into the brain may allow for the use of reduced intensity conditioning to achieve substantial beMφ engraftment in patients. The ability to achieve engraftment less radiation and/or chemotherapy provides an obvious benefit to patients undergoing HC transplantation.

In a fifth aspect, the present invention provides a method of engrafting hematopoietic-derived macrophages in the brain of a subject undergoing HC transplantation comprising subjecting the subject to a transplant conditioning regimen and administering a microglia depleting agent. Conditioning regimens that may be used with the present invention are any known in the art and include, irradiation, chemotherapy, or a combination thereof. In some embodiments of this aspect of the invention, the subject is subjected to the conditioning regimen prior to the administration of the microglia depleting agent. In other embodiments, the subject is subjected to the conditioning regimen concurrently with the administration of a microglia depleting agent. In yet other embodiments of this aspect of the invention, the subject is subjected to the conditioning regimen after the administration of a microglia depleting agent.

The inventors have discovered that beMφ are a unique cell type, distinct from microglia, and while capable of taking up long-term residence in the CNS, they maintain a unique transcriptional and functional identity. Indeed, this may help explain the reported therapeutic roles for beMφ (Chen et al., 2010; Derecki et al., 2012; Hsiao et al., 2012; Krivit et al., 1999; Krivit et al., 1995; Platt and Lachmann, 2009; Walkley et al., 1994), and suggests that beMφ may not only replace dysfunctional microglia, but may in fact provide unique therapeutic benefits based on their unique identity and functional profile.

Notably, the inventors have determined that beMφ and microglia each have a specific transcriptional/genetic signature. These core genetic signatures may be used to define and identify beMφ and microglia and/or differentiate between the two. In particular, the inventors have found that microglia bear a 52-gene signature (Mg-52) and beMφ bear a 50-gene signature (beMφ-50). The Mg-52 signature is specific to adult microglia, and the beMφ-50 signature does not correlate to any microglia developmental programs; accordingly these signatures may be used for the detection of microglia vs. non-microglia.

Thus, in a further aspect, the present invention provides a method of detecting beMφ cells in a cell population comprising analyzing the cell population for the beMφ-50 signature, wherein the presence of the beMφ-50 signature indicates that beMφ cells are present in the cell population. In a yet further aspect, the present invention provides a method of detecting microglia in a cell population comprising analyzing the cell population for the Mg-52 signature, wherein the presence of the Mg-52 signature indicates that microglia cells are present in the cell population. In a still further aspect, the present invention provides a method of differentiating between beMφ and microglia cells in a cell population comprising analyzing the genetic signature of the cell population, wherein the presence of the beMφ-50 signature indicates the presence of beMφ cells in the cell population and wherein the presence of the Mg-52 signature indicates the presence of microglia cells in the cell population. In these aspects of the invention, the cell population may be analyzed for the genetic signature of interested in accordance with the methods and examples set forth herein.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

EXAMPLES

Example 1—Materials and Methods

Animal Experiment Approval

All experiments were approved by the Institutional Animal Care and Use Committee (IACUC) of the University of Virginia.

Mice

Mice were initially purchased from the Jackson Laboratory and subsequently maintained and bred in-house under standard housing conditions (12 hour light/dark cycle and fed ad libitum). All mice were on a C57BL/6J background and both males and females were used unless stated otherwise. Strains used were C57BL/6J, C57BL/6-Tg(UBC-GFP)30Schaa, B6.129P2(C)-Cx3cr1$^{tm2.1(cre/ERT2)Jung}$/J and B6.Cg-Csf1r$^{tm1-2.1JwP}$/J. Cx3cr1$^{CreER/+}$::Csf1r$^{Flox/Flox}$ mice were generated by breeding Cx3cr1$^{CreER/+}$::Csf1r$^{Flox/Flox}$ mice with Cx3cr1$^{+/+}$::Csf1r$^{Flox/Flox}$ mice. For experiments using tamoxifen, mice were fed TD.130856 at 250 mg/kg diet (purchased from Harlan) starting at 4 weeks after birth, or as otherwise specified in figures. Experimental groups were blinded prior to beginning the experiment and remained blinded until the end.

Irradiation and Bone Marrow Transplant

Mice were γ-irradiated with a lethal dose of 1000 rad. Four hours post irradiation, mice were intravenously injected with $5 \times 10^6$ bone marrow cells. Mice were given water supplemented with trimethoprim-sulfamethoxazole for two weeks and monitored daily for the first 4 days. A lead shield was placed over the head during irradiation in some experiments, as indicated.

Tissue Collection

Mice were euthanized with Euthasol then transcardially perfused with 0.01 M PBS containing 5u/ml heparin. Blood was collected from the retinal artery after removing the eye and placed in heparinized tubes. For immunohistochemistry, brains were carefully removed and dropped fixed in 4% paraformaldehyde for 48 hours. Brains were then washed with PBS and stored at 4° C. until further processing. For isolating cells, brains were harvested and immediately processed as described below. Intestinal cell suspensions were prepared as previously described (Cronk et al., 2015). Briefly, the entire length of the small intestine was excised and opened longitudinally. Luminal contents were washed in Ca/Mg-free PBS, chopped in 2.5 cm pieces and placed in conical tubes containing 30 mL HBSS, 5% FBS, and 2 mM EDTA. The tubes were shaken at 37° C. and 250 RPM for 20 minutes, after which the intestines were strained through a nylon mesh and washed again under the same conditions. After the last wash, the intestines were transferred into 20 mL of HBSS containing Collagenase VIII (Sigma, 900 U/mL) and DNase-I (Sigma, 40 U/mL), then shaken for 15 minutes at 200 RPM to digest. After the incubation, the tubes were vortexed thoroughly and the resulting cell suspension passed through 70 um cell strainers into clean tubes. The cells were washed twice with cold HBSS, 5% FBS, and 2 mM EDTA and centrifuged at 4° C., 425 RCF, for 5 m. Following the last wash, the supernatant was decanted and the pellet was resuspended in FACS buffer containing 0.01 M PBS, 1% BSA, 2 mM EDTA, and 0.1% sodium azide and prepared for FACS analysis.

Flow Cytometry

After tissue collection (as described above), cells were incubated with flow cytometry antibodies at 4° C. for 30 min in a total volume of 200 µl flow cytometry buffer (PBS containing 0.1% sodium azide and 1% BSA), washed with 5 ml flow cytometry buffer, pelleted at 300 RCF, decanted, and analyzed on a Gallios flow cytometer (Beckman Coulter). Antibodies were purchased from BD Pharmingen except for CD115 (BioLegend).

Immunohistochemistry

Brains were collected as described above and cryoprotected in 30% sucrose. After freezing in O.C.T. compound (Sakura Finetek) 40 µM sections were cut on a cryostat (Leica). Floating sections were stored in PBS containing Azide (0.02%) until further processing. For immunohistochemistry, brain sections were permeabilized with PBS containing 0.5% Triton-X100 then blocked with 10% chicken serum in PBS containing 0.05% Triton-X100 for 1 hour. Sections were then incubated overnight with primary antibody in PBS containing 2% chicken serum. Primary antibodies included Rabbit anti-GFP (1:1000 Abcam), Goat anti-Iba1 (1:300; Abcam), Rabbit anti-Iba1 (1:300; Wako), Rabbit-anti Ki67 (1:500, Abcam), and Rabbit anti-P2ry12 (1:10,000 generous gift from Oleg Butovsky). After incubating primary antibody, sections were washed 3 times then incubated with fluorescently conjugated secondary antibodies (1:1000) in PBS containing 0.05% Triton-X100 and 2% chicken serum for 1 hour. Sections were then washed 3× with PBS containing 0.05% Triton-X100. DAPI was added to the second wash to stain DNA containing nuclei. Sections were then mounting on microscope slides with Aquamount. All images were collected on a Leica SP8 confocal microscope or Leica wide field microscope.

BrdU Proliferation Assay

BrdU injections and analysis was performed as previously described (Lu et al., 2011). Briefly, mice were injected twice (i.p.) with 50 mg/mg BrdU, with 2 hours between each injection. Brains were analyzed by immunohistochemistry 24 hours after the last BrdU injection.

Cell Sorting

To FACS sort microglia and beMφ, brains were collected after euthanization and systemic perfusion with PBS, then meninges were removed. Brains were physically minced and incubated in a 15 mL tube in 5 ml HBSS containing Mg and Ca, 2 mg/ml papain, 50 u/ml DNASE-I (Sigma) and Glutamax (Invitrogen) at 37° C. for 15 minutes. After gentle trituration, the brains were incubated at 37° C. for an additional 15 minutes, triturated, incubated at 37° C. for an additional 15 minutes, and triturated a third time. Following this, the tubes were filled with DMEM/F12 containing 10% FBS and filtered through a 70 µM cell strainer. Cells were pelleted at 300 RCF and sorted as follows. Cells were incubated with CD11b+ microglia magnetic selection beads according to manufacturer's protocol (Miltenyi). Cells were then positively selected by AutoMACS and used for downstream applications or FACS sorted by gating on live cells by DAPI exclusion (DAPI-negative cells, high side scatter exclusion, singlet events, $CD45^{Lo}$, $CD11b^+$, and either $GFP^-$ (microglia) or $GFP^+$ (beMφ). Monocytes were isolated from bone marrow using mouse bone marrow monocyte selection beads and sorted on LS magnetic columns according to manufacturer's protocol (Miltenyi). Sorted monocytes were at least 95% pure monocytes ($CD11b^+Ly6C^{Hi}CD115^+$) by flow cytometry.

RNA Sequencing and qrtPCR

RNA was isolated from FACS sorted microglia using an RNAeasy mini kit (Qiagen). Each sample used for RNA-seq was pooled from 3 or 4 total mice per sample. For qrtPCR, cDNA was generated using High Capacity cDNA kit (Applied Biosystems) and Csf1r gene expression was analyzed with the Mm00432691_m1 TaqMan Gene Expression assay. For RNA sequencing, all post-processing (including linear RNA amplification and cDNA library generation) and sequencing was performed by Hudson Alpha Genomic Services Laboratory.

Evans Blue BBB Permeability Assay

To test for BBB permeability, mice were injected i.p. with Evan's blue (13.3 µl/g of a 2% Evans blue solution dissolved in PBS) and samples were collected 1 hour post-injection. Mice were euthanized by Euthasol, perfused with ice cold PBS, and brains were removed. One-half of each brain was homogenized in 1 ml of PBS and mixed with one volume of 50% trichloroacetic acid, then incubated overnight at 4° C. to precipitate out proteins and other particulates. Samples were centrifuged at 15,000 g for 30 min, 4° C. Supernatants were analyzed by 96-well plate reader at 620 nm (Multiskan FC, Fisher Scientific) and a standard curve was generated using known concentrations of Evans Blue dye in PBS mixed 1:1 with 50% trichloroacetic acid.

Parabiosis

Surgery for parabiosis was performed as previously described (Radjavi et al., 2014). Female UBC-GFP mice were paired to $Cx3cr1^{CreER/+}::Csf1r^{Flox/Flox}$ mice or Cre-negative controls matched for age, sex, and weight. After parabiosis surgery, mice were allowed 3 weeks to recover prior to a 12 week tamoxifen treatment.

Behavior

Behavioral testing was performed as previously described (Filiano et al., 2016; Radjavi et al., 2014). Before all behavior testing, mice were acclimated to the testing room for 1 hour. Testing schedules were balanced for genotype and the observer was blinded to all conditions. Mazes were cleaned with 70% ethanol between trials and all behavioral assays were performed during the light hours avoiding 1 hour after and before the lights turned on and off.

Plus Maze:

Mice were place into the center hub of the plus maze and were free to explore for 5 minutes. Movement was calculated with TopScan (CleverSys) and data were represented as a percent of time spent in the open arms during the 5 minute trial.

Open Field:

Mice were placed into an open field (35 cm×35 cm) and were free to explore for 15 minutes. Movement was monitored via TopScan and data were represented as percent time spent in the center of the box (23 cm×23 cm) during the 15 minute trial.

Sociability:

Social behavior was tested using the 3-chamber assay. Mice were placed into the center chamber of a 3-chamber social box and were free to explore all 3 rooms for 10 minutes per phase. For the habituation phase, empty wire cages (Spectrum Diversified Designs) were placed in the 2 outer rooms. After the initial habituation phase, the mice were returned to the center room for the social phase and a novel mouse was placed under one cup (8-10-week-old male habituated to the cup) and a novel object was placed under the other cup. Tracking was scored with TopScan and time spent investigating around each cup was quantified.

Rotarod:

Motor behavior was tested with an accelerated rotarod (MedAssociates). Mice were placed on an accelerating rotarod that accelerated from 4.0 to 40 rpm over 5 minutes. The latency of the mouse to fall off the rod was monitored via infrared beams. Mice were given 6 trials with a 4-hour inter-trial interval between trials 3 and 4.

Morris Water Maze:

Cognitive function was tested with the water maze. For the acquisition phase, mice were placed in a 100 cm pool of opaque water with a hidden platform 1 cm under the surface. Mice were given 3 trials per day (max 60 seconds) to find the platform with 30 minutes between each trial. This was repeated for 4 days. One the fifth day, for the probe trial, the platform was removed and mice were given 60 seconds to explore the maze. Video tracking of movement was performed with an EthoVision tracking system. For the acquisition phase, data were represented as latency to reach the platform. For the probe trial, data were represented as time spent in the quadrant that previously contained the platform.

Laser-Burn Injury

Brain macrophages were imaged by multiphoton microscopy. To target microglia, $Cx3cr1^{CreER/+}$::Ai6 were irradiated with head shielding and given bone marrow from a wild-type donor mouse. To target beMφ, wild-type mice were irradiated and given bone marrow from a $Cx3cr1^{GFP/+}$ donor mouse. After 4 weeks of recovery, mice were fed tamoxifen for 4 weeks to pulse label macrophages then placed back on normal chow. After 4 weeks on normal chow, all mice were fed PLX5622 for 2 weeks to clear out the brain macrophage pool and allowed to recover for 6 weeks prior to imaging. For imaging, mice were anesthetized with ketamine/xylene (i.p.). Two-photon laser injury was performed by focusing a two-photon laser beam in the superficial layer of the cortex (about 50 µm deep) through a thinned intact skull as previously described (Davalos et al., 2005). Briefly, a 780 nm two-photon laser (Chameleon Ultra II tunable Ti:Sapphire laser—Coherent) with a laser power of 60-80 mW was applied to a region of interest of 20 µm of diameter for approximately 30 sec (the efficiency of the injury was visualized by the bright autofluorescence sphere in the region of interest. The area was image for 30 min prior to the laser injury and 30 min following the laser injury. Images were acquired using a×25 water immersion objective with 0.95NA and external HyD non-descanned detectors (Leica). Four-dimensional imaging data were collected by obtaining images from the x, y, and z planes over time.

Image Analysis

Automated image analysis algorithms were developed and implemented in the Virginia Image and Video Analysis laboratory (Acton). The software was written in the Matlab (Mathworks, Natick, Mass.) environment.

Process Detection:

Microglia and engrafted macrophage processes were detected from the images using area morphology implemented via connected filters (Acton, 2001; Acton and Mukherjee, 2000). Such connected filters have advantages over traditional filters in that they are edge preserving and do not depend on binarized versions of the image. The processes were detected that had a 2D area (observed via maximum intensity projection) within a range of 15 $\mu m^2$ to 75 $\mu m^2$ and sufficient contrast with the background (>4% of intensity range). The positions of the processes were recorded by computing the region centroids.

Process Tracking:

Individual process locations were tracked temporally from frame to frame by finding a correspondence between detections (Scott Thomas Acton, 2006). The correspondence was determined by spatial proximity, consistency in direction of motion, and similarity in size. Group motion (and corresponding velocity) of the processes was computed using a dynamic Sholl analysis. The Sholl diagram was centered at the center of the burn site and consisted of five annuli of ring width of 17 µm. Groups of processes were tracked (in maximum intensity projection images) from the time of maximum population in the fifth annulus to the time of maximum population (of detected processes) in the third annulus (which was just outside the perimeter of the burn). This group tracking provided an overall speed computation that was robust to false positives and missed detections in the process detection task.

LPS Challenge

To determine transcriptional and morphological changes of microglia and beMφ to an insult, mice were given a peripheral LPS challenge. Mice were first irradiated and given BMT with UBC-GFP bone marrow. To target microglia, head shielding was applied during irradiation in some mice. After 1 week of recovery, mice were treated with PLX 5622 for 2 weeks to deplete the brain macrophage niche then placed on standard chow for 6 weeks. Mice were injected with 50 µg LPS or saline (i.p.). 6 hours later, brains were removed and macrophages sorted by MACS on CD11B beads as described above.

RNA-Seq and Functional Analysis

The Gene Expression Omnibus (GEO) accession numbers for RNA-seq data generated for this publication are GSE84819, GSE108569, and GSE108575. All other previously published datasets utilized are GSE68376, GSE15907, GSE63340, GSE75246, GSE99078. The raw sequencing reads (FASTQ files) went through two stages of preprocessing to remove low quality reads and bases. First, they were chastity filtered, which removes any clusters that have a higher than expected intensity of the called base compared to other bases. Then they were trimmed with Trimmomatic (Bolger et al., 2014) to remove low quality bases (minimum read length after trimming=36). After preprocessing, the quality of the reads was evaluated using FastQC (Andrews, 2010), and after passing quality control (QC), were aligned to the UCSC mm9 genome (Harrow et al., 2012) using the splice-aware read aligner STAR (Dobin et al., 2013). The quality of the alignments was next assessed by SAMStat (Lassmann et al., 2011), and any low quality alignments were removed with samtools (Li et al., 2009) (MAPQ<10). Next, the number of reads aligning to each gene was quantified with HTSeq (Anders et al., 2015), and then the Bioconductor package (Love et al., 2014). DESeq2 was used to normalize the raw counts, perform exploratory analysis (e.g., PCA), and differential expression (DE) analysis. Before DE analysis of BMT/PLX dataset, surrogate variable analysis (Leek and Storey, 2007) was used to identify and adjust for latent sources of unwanted variation as implemented in the sva package (Leek et al., 2012). The p-values from the DE analysis were corrected for multiple hypothesis testing with the Benjamini-Hochberg false discovery rate procedure. Heatmaps were generated with the R package pheatmap (Kolde, 2015) and UpSet plots (Lex et al., 2014) were created with the R package UpSetR (Gehlenborg, 2016). The functional terms enriched in beMφ and microglia for our RNA-seq datasets were determined with gene set variation analysis (GSVA) (Hanzelmann et al., 2013). The gene sets used for this analysis were from the Biological Processes arm of the Gene Ontology (GOBP) (Ashburner et al., 2000; The Gene Ontology, 2017).

Microarray Analysis

All of the microarrays were analyzed using a combination of the affy (Gautier et al., 2004), oligo (Carvalho and Irizarry, 2010), and limma (Ritchie et al., 2015) packages from Bioconductor packages. For the Affymetrix arrays, the expression values for each probe set was extracted using the Robust Multichip Average (RMA) methodology (Irizarry et al., 2003). For the Agilent arrays, the probes were background corrected using a normal-exponential convolution model (as implemented in limma) (Silver et al., 2009) and quantile normalized. Replicate probes were summarized using the mean.

Signature Creation

To create the Mg-52 signature, we first identified the differentially up-regulated genes in microglia vs. beMφ in all three of the "Kipnis datasets": the genetic model, traditional BMT, and BMT/PLX RNA-seq. To be called significant, a gene needed to have a fold change greater than 1.5 and a corrected p-value less than 0.05. These criteria for significance were used to identify all differentially expressed genes hereafter. Next, we identified the differentially up-regulated genes in microglia vs. peripheral myeloid cell types (9 cell types in total) from the Lavin RNA-seq dataset. The cell types in this dataset were peritoneal Mφ, small intestine Mφ, large intestine Mφ, monocytes, Kupffer Mφ, red pulp Mφ, alveolar Mφ, and neutrophils. The Mg-52 signature was defined as the 52 genes that were 1) up-regulated in microglia in all three of the Kipnis datasets, 2) up-regulated in 8/9 microglia vs. peripheral myeloid cell comparison from the Lavin dataset, and 3) included in a gene set that was functionally enriched in microglia in at least one of the Kipnis datasets. To create the beMφ-50 signature, we first identified the differentially up-regulated genes in beMφ vs. microglia in all three of the Kipnis datasets and the differentially up-regulated genes in the nine myeloid cell types vs. microglia in the Lavin RNA-seq dataset. The beMφ-52 signature was defined as the 50 genes that were 1) up-regulated in beMφ in all three of the Kipnis datasets, 2) not up-regulated peripheral myeloid cells from the Lavin dataset, and 3) included in a gene set that was functionally enriched in beMφ in at least one of the Kipnis datasets.

Signature Detection

The signatures were detected in the various transcriptomic data sets using a competitive gene set test called CAMERA (Wu and Smyth, 2012) (part of the limma package). The inter-gene correlation was set to 0.01. To use CAMERA with the RNA-seq data, the raw counts needed to be transformed and normalized with the voom function (Law et al., 2014). This was not necessary for the microarray data. CAMERA returns both a test statistic and an FDR-corrected p-value. The test statistic was used as an enrichment score, with larger values of the statistic corresponding to a greater enrichment of the signature. To ensure the fidelity of the signature detection, we used a stringent corrected p-value threshold of 1E-3.

Example 2—CSFR1 Antagonists Potentiate Engraftment of Hematopoietic-Derived Macrophages in the Brain We utilized the Csf1r inhibitor PLX5622 in chow, to eliminate irradiation-damaged, yet still viable, microglia. Mice were given BMT with UBC-GFP bone marrow with or without head covering during irradiation, followed by 1 week of recovery, 2 weeks of chow containing PLX5622, and finally 6 weeks of recovery on standard chow. Mice with head covering had minimal GFP+ beMφ engraftment and had effectively repopulated the CNS with endogenous microglia with minimal beMφ engraftment, consistent with previously published data (Elmore et al., 2014). However, mice that had received whole body irradiation demonstrated robust engraftment of GFP+ beMφ. Thus, proof of concept that PLX3397 or PLX5562 can potentiate engraftment of hematopoietic-derived macrophages into the brains of mice when used as part of a protocol that clears the microglial niche was established.

Example 3—Chronic Microglia Depletion Drives Engraftment of Brain Engrafting Macrophages (beMφ)

We tested the ability of beMφ to engraft, independent of irradiation, in a brain niche characterized by chronic microglia depletion. To deplete microglia chronically, we used Cx3cr1$^{CreER/+}$::Csf1r$^{Flox/Flox}$ mice fed tamoxifen chow to chronically excise Csf1r (the gene encoding colony stimulating factor 1 receptor, which is critical for microglia survival) from cells expressing Cx3cr1, which in the brain is restricted to microglia (Goldmann et al., 2013; Li et al., 2006; Yona et al., 2013).

Figure 1B:
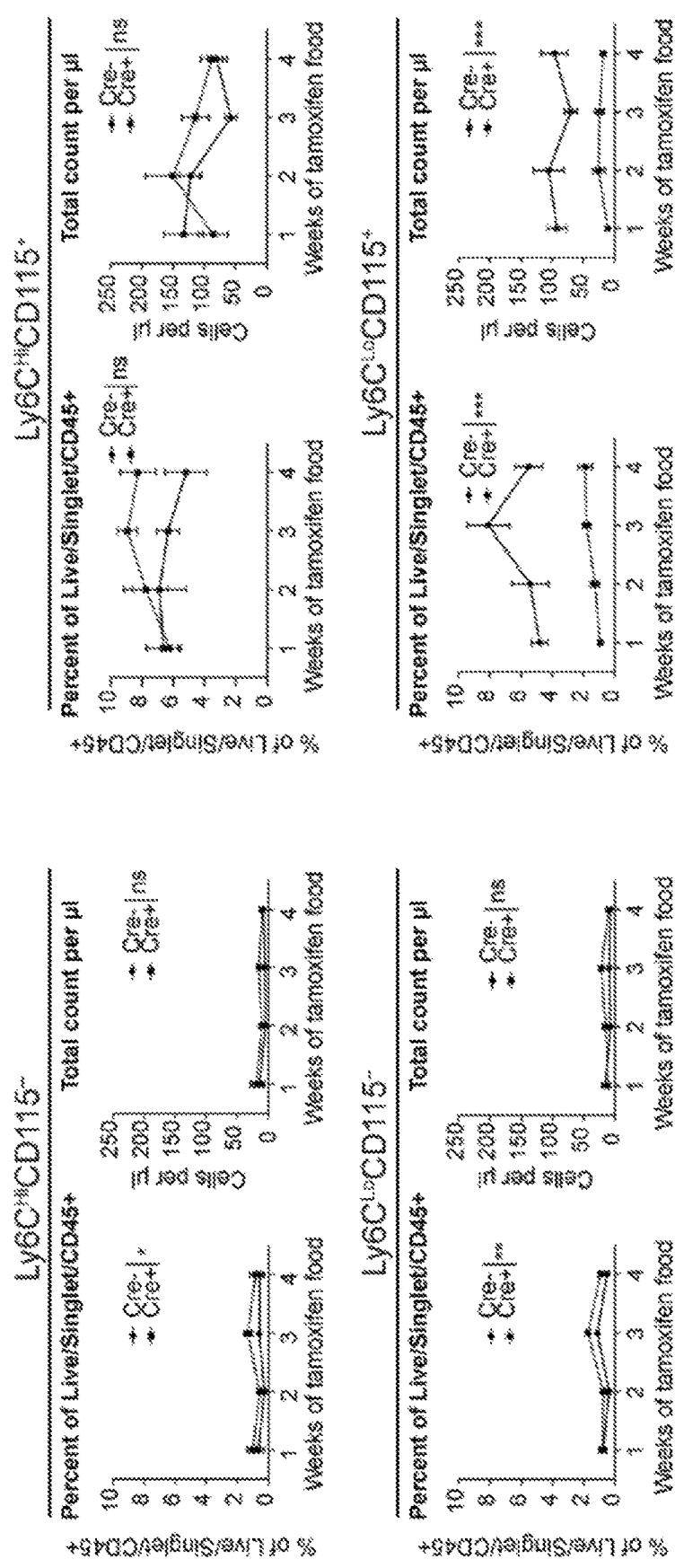

Prior to analyzing the brain, we assessed the peripheral immune system, which contains many cells that express Cx3cr1. Cx3cr1$^{CreER/+}$::Csf1r$^{Flox/Flox}$ mice treated with tamoxifen demonstrated chronic deficiency in Cx3cr1$^+$ lamina propria intestinal macrophages (FIG. 1A). While Cx3cr1$^{lo/net}$Ly6C$^{hi}$ monocytes did not experience significant changes upon tamoxifen treatment, Cx3cr1$^{hi}$Ly6C$^{lo}$ monocytes were severely depleted in these mice (FIG. 1B), consistent with expression of Cre driven by the Cx3cr1 promoter.

We then moved on to analyze the brain. While no differences were observed in microglia counts between Cx3cr1$^{CreER/+}$::Csf1r$^{Flox/Flow}$ and Cx3cr1$^{+/+}$::Csf1r$^{Flox/Flox}$ animals fed control chow (FIG. 2A), one week on a tamoxifen diet induced an approximate 25% reduction of microglia throughout the brain, which was maintained for the duration of tamoxifen treatment (FIG. 2B). When Csf1r levels were analyzed after twelve weeks on a tamoxifen diet, both protein and gene expression were reduced, but not completely eliminated, as compared to Cre-negative controls (FIG. 2C and FIG. 2D), consistent with partial microglia depletion. To help explain why microglia were only partially depleted, we immunostained for Ki67 and assessed the incorporation of BrdU. We found that microglia were Ki67+ and BrdU+ in Cx3cr1$^{CreER/+}$::Csf1r$^{Flox/Flox}$ mice but not Cx3cr1$^{+/+}$::Csf1r$^{Flox/Flox}$ mice fed tamoxifen chow. These data demonstrate that the microglia niche begins to proliferate in response to inducible Csf1r excision, suggesting that microglia loss is countered by proliferation of the remaining Csf1r-expressing microglia, or that signaling through another growth factor receptor is capable of driving microglia proliferation.

Figure 2E:
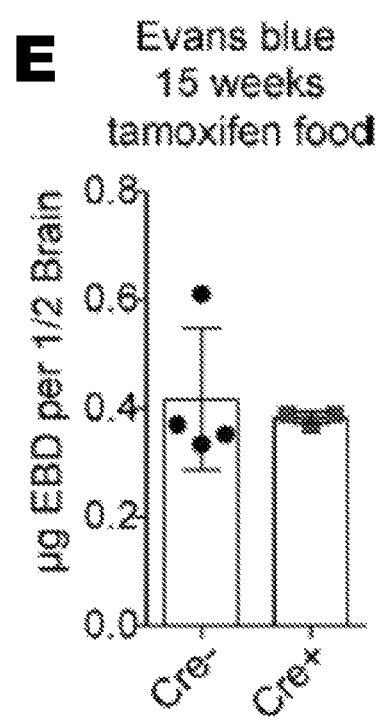
FIG. 2. Partial microglia depletion leads to beMφ engraftment independent of irradiation. (A) Counts per field of microglia in $Cx3cr1^{CreER/+}$ or $Cx3cr1^{+/+}::Csf1r^{Flox/Flox}$ mice not treated with tamoxifen (n=3 mice/group, Two-way ANOVA with Tukey's multiple comparisons post-test, not significant (ns)). (B) Deleting Csf1r from microglia results in approximately 25% chronic reduction of microglia throughout the brain (n=3-4 mice per group for each time point; representative of two experiments). (C) Gene expression by qRT-PCR of CD115/Csf1r on sorted microglia (n=3 per group; two-tailed Student's t test,  p<0.01; performed once). (D) Histogram and MFI of CD115/Csf1r expressed on sorted microglia (n=5 per group; two-sided Student's t test, * p<0.001; representative of two independent experiments). (E) Quantification of Evan's blue in brains of $Cx3cr1^{+/+}::Csf1r^{flox/flox}$ and $Cx3cr1^{CreER/+}::Csf1r^{flox/flox}$ mice fed tamoxifen diet for 15 weeks (n=4 and 3 mice per group, two-tailed Student's t test, not significant; performed once). (F-J) Percentage of B cells (F), T cells (G), neutrophils (H), $Ly6c^{hi}$ monocytes (I), and $Ly6c^{lo}$ monocytes (J; n=4-6 mice per group; experiment performed once). Error bars represent±SEM. (K-P) No differences in behavior were observed in mice containing beMφ (Cre+). $Cx3cr1^{CreER/+}::Csf1r^{Flox/Flox}$ mice and Cre-negative controls underwent BMT with head shielding. After recovery, mice were treated with tamoxifen for 12 weeks then placed back on a regular diet for 4 weeks prior to behavioral testing. Mice were tested on the (K) plus maze (not significant, two-tailed Student's t-test; n=24, 23; pooled data from two independent cohorts), (L) open field (not significant, two-tailed Student's t-test; n=24, 23; pooled data from two independent cohorts), (M) 3-chamber social assay (not significant for genotype and * p<0.05 for social variable, two-way repeated measures ANOVA with Sidak's post hoc; n=15; pooled data from two independent experiments), (N) rotarod (not significant for genotype, two-way repeated measures ANOVA; n=9, 8; experiment performed once), and (O) water maze (not significant for acquisition, two-way repeated measures ANOVA and not significant for probe trial, two-tailed Student's t-test; n=9, 8; performed once). (P) Quantification of brain macrophages from mice in behavior assays by flow cytometry. Mice were analyzed after behavior assays were complete, at least 8 weeks after they had been placed back on regular diet. Brains of Cre-positive mice contained 48.2%±14.2 SEM beMφ (GFP+) out of the total CD45/CD11b$^+$ cells (not significant, two-tailed Student's t-test; n=3 samples per cell type with 3-4 mice pooled per sample; performed once).

Together, these data demonstrated that inducible deletion of Csf1r in microglia leads to chronic, partial microglia loss, leaving a partially unfilled niche. We could therefore use this model to test whether the presence of a niche (formed without irradiation) that cannot be filled by microglia, could allow beMφ engraftment. Importantly, we did not detect increased BBB permeability in tamoxifen-treated Cre-positive as compared to Cre-negative mice (FIG. 2E).

We first injected 95% pure Ly6C$^{hi}$CD115$^+$ sorted bone marrow monocytes expressing GFP intravenously into Cx3cr1$^{CreER/+}$::Csf1r$^{Flox/Flox}$ mice on a tamoxifen diet. Starting one-week post tamoxifen, mice were given three weekly intravenous injections of GFP$^+$ monocytes. Mice were analyzed 1 or 9 weeks after the final monocyte transfer (4 or 12 weeks after tamoxifen initiation). The brains of Cre-positive animals contained ramified GFP+ beMφ, while none were observed in brains of Cre-negative mice. These results show that in the context of chronic microglia deficiency (and without CNS irradiation, infection, or BBB compromise) circulating monocytes can engraft into the CNS and persistently fill the available niche created by depleted microglia, as cells were still present 9 weeks after the final cell transfer.

It is possible that sorted bone marrow monocytes possess a unique ability to engraft the CNS that is not possessed by circulating blood monocytes. To confirm that circulating cells are capable of engrafting the CNS, we used parabiotic mice. Cre-negative or Cre-positive mice were parabiotically joined to UBC-GFP mice, and placed on a tamoxifen diet for 12 weeks. As expected, Cre-negative mice had no detectable GFP+ cells in their brains, whereas Cre-positive mice contained GFP+ ramified beMφ in the parenchyma. Since the bone marrow niche remains undisturbed in parabiosis, these results provide evidence that circulating monocytes (or at a minimum, circulating leukocytes) indeed possess the ability to engraft the brain and become beMφ when the microglia-vacant niche is present.

While monocyte transfer and parabiosis demonstrated that beMφ can and will engraft the microglia-depleted brain without irradiation, these experiments did not reveal the potential extent of beMφ engraftment. To understand the full extent of peripheral-derived engraftment into the CNS in tamoxifen-treated Cx3cr1$^{CreER/+}$::Csf1r$^{Flox/Flox}$ mice, we decided to completely replace the peripheral immune system with GFP-expressing cells. To this end, we performed BMT with lead shielding of the head, a well-established technique to prevent beMφ engraftment after BMT (Butovsky et al., 2006; Butovsky et al., 2007; Derecki et al., 2012; Rolls et al., 2008; Shechter et al., 2009). Five weeks after BMT, nearly every circulating immune cell (except T cells, which is a known phenomenon (Bosco et al., 2010)) was GFP+, including nearly 100% of monocytes (FIGS. 2F-J).

We then assessed beMφ engraftment at two, four, or twelve weeks after tamoxifen. We could only detect rare GFP$^+$ Iba1$^+$ ramified beMφ after 2 weeks, primarily in circumventricular regions, but after four weeks, the circumventricular regions of these mice had considerable engraftment of beMφ. Interestingly, we observed that while GFP+ cells could be found in the choroid plexus and ventricle walls of all mice, ramified GFP$^+$ Iba1$^+$ beMφ were only present in the brain parenchyma in Cx3cr1$^{CreER/+}$::Csf1r$^{Flox/Flox}$ mice. After twelve weeks, we found GFP$^+$ Iba1$^+$ macrophage engraftment throughout the brains of Cx3cr1$^{CreER/+}$::Csf1r$^{Flox/Flox}$ animals, as opposed to their Cre-negative counterparts, in which no ramified GFP+ cells were observed anywhere in the brain parenchyma. Further, if we irradiated the entire mouse (including the head) beMφ engraftment into Cx3cr1$^{CreER/+}$::Csf1r$^{Flox/Flox}$ mice was greatly accelerated as compared to Cre-negative controls. This suggests that while CNS irradiation induces beMφ engraftment, this is substantially enhanced by impairment of microglia self-renewal by deletion of Csf1r.

We next set out to interrogate whether or not beMφ affect brain function using a battery of behavioral assays. Head-covered BMT was performed in Cx3cr1$^{CreER/+}$::Csf1r$^{Flox/Flox}$ and Cx3cr1$^{+/+}$::Csf1r$^{Flox/Flox}$ mice as described above, and mice were fed a tamoxifen diet for 12 weeks, followed by 4 weeks of control chow to eliminate the potential effects of tamoxifen on behavior. We found no difference in any behavioral assays tested, such as elevated plus maze (FIG. 2K), open field (FIG. 2L), sociability (FIG. 2M), rotarod (FIG. 2N), or Morris water maze (FIG. 2O). Importantly, we found that Cre-positive mice had an average of 48% GFP+ beMφ out of all CNS macrophages/microglia at the conclusion of behavioral testing, at which point mice had been on control chow for a minimum of 8 weeks (FIG. 2P). Together, these results suggest that even with significant microglia replacement by beMφ, overall brain function is not affected.

Example 4—beMφ are Transcriptionally Distinct from Microglia

Figures 3A, 3B:
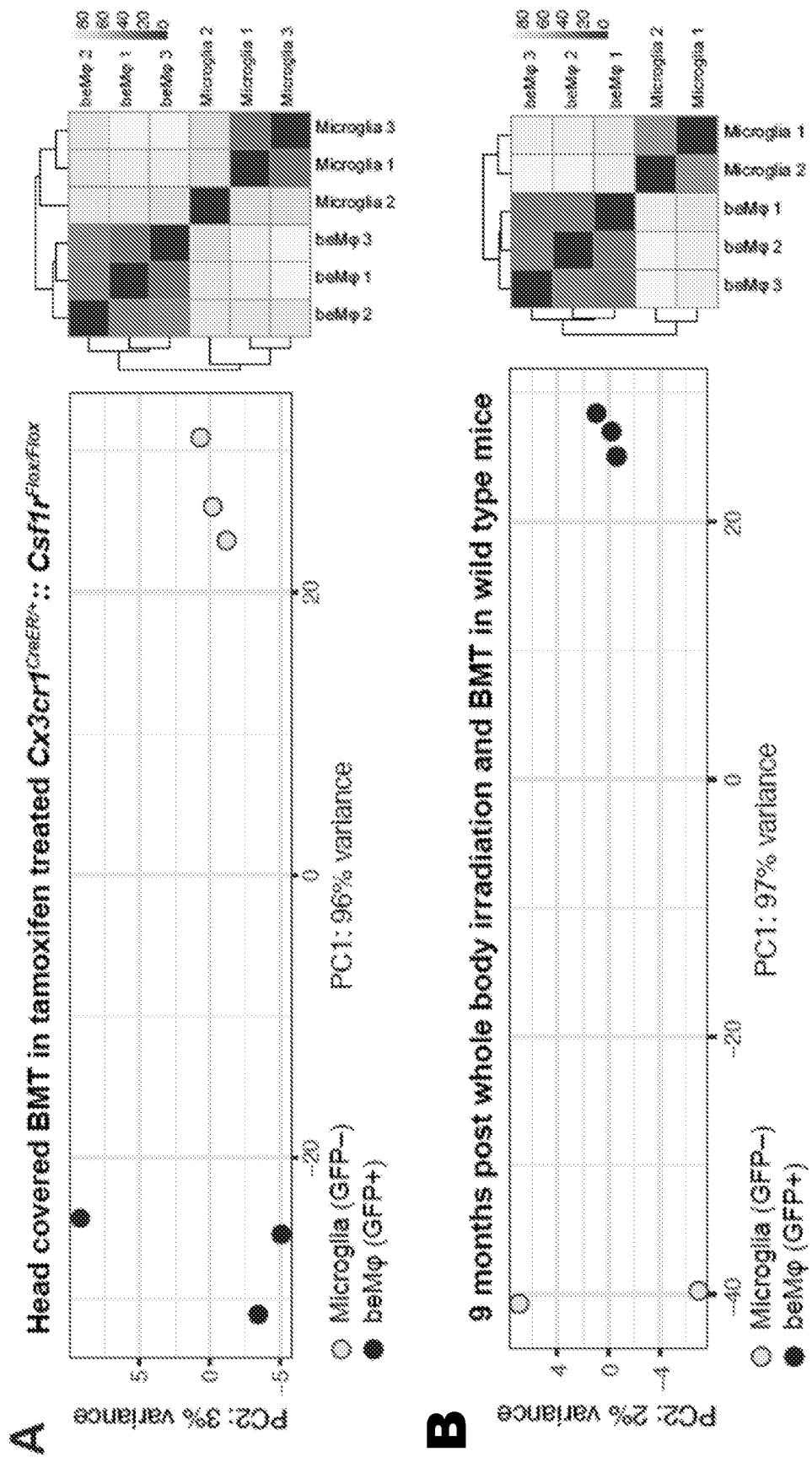
FIG. 3. (A) PCA plot and heatmap of distance between samples for beMφ and microglia in the $Cx3cr1^{CreER/+}::Csf1r^{Flox/Flox}$ model with head covered BMT and tamoxifen treatment. Mice were treated with tamoxifen for 12 weeks, followed by a minimum of 8 weeks on control chow (each dot represents a pooled sample from at least 3 mice). (B) PCA plot and heatmap of distance between samples for the beMφ and microglia when using traditional BMT (each dot represents a pooled sample from at least 3 mice). (C) PCA plot and heatmap of distance between samples for beMφ and microglia when using BMT/PLX5622 (each dot represents a pooled sample from at least 3 mice).

We next set out to assess whether beMφ are an independent class of brain macrophage with a unique functional and transcriptomic profile. To this end, we decided to perform RNA-seq on beMφ and microglia in three unique models of beMφ engraftment. First, we sorted live CD45$^+$CD11b$^+$ and either GFP-negative (microglia) or GFP-positive (beMφ) cells from the same brains of tamoxifen-treated Cx3cr1$^{CreER/+}$::Csf1r$^{Flox/Flox}$ mice (mice were given UBC-GFP BMT with head-covering and treated with tamoxifen 12 weeks, followed by at least 8 weeks on regular chow. Microglia and beMφ were FACS sorted from the same brains, and then RNA-seq followed by differential analysis was performed (n=3 microglia samples, pooled from 3 total mice for each sample, and n=3 beMφ samples, pooled from 3 total mice for each sample; performed once)). Microglia and beMφ cluster strongly by cell type, with cell type accounting for 96% of the transcriptional variance (FIG. 3A). Compared to microglia, beMφ had 1512 differentially upregulated and 1598 differentially downregulated genes.

In our second model of beMφ engraftment, we replicated classic beMφ engraftment models by performing whole body irradiation and BMT with UBC-GFP bone marrow. We then allowed cells to engraft and remain for 9 months, and sorted beMφ and microglia from the same brains. Then RNA-seq followed by differential expression analysis was performed (n=2 microglia samples, pooled from 4 total mice for each sample, and n=3 beMφ samples, pooled from 4 total mice for each sample; performed once). Again, we found that cell type accounted for the large majority of variance (97%) (FIG. 3B), and when compared to microglia, beMφ had a large number of differentially upregulated (2008) and differentially downregulated genes (1596).

Figure 3C:
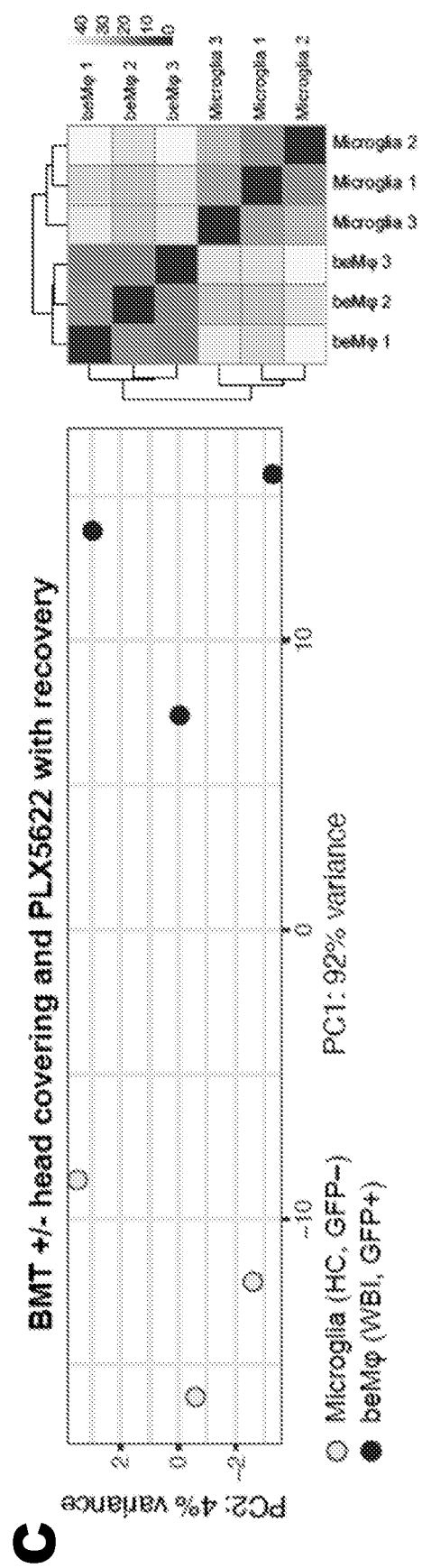

Our third model (see Example 2) was designed to take advantage of the synergistic effect on engraftment we had observed with the combination of CNS irradiation and Csf1r deletion in microglia. Instead of Csf1r deletion using our genetic model, we utilized the Csf1r inhibitor PLX5622 in chow, to eliminate the irradiation-damaged, yet still viable, microglia. Mice were given BMT with UBC-GFP bone marrow with or without head covering during irradiation, followed by 1 week of recovery, 2 weeks of chow containing PLX5622, and finally 6 weeks of recovery on standard chow. In this model, mice with head covering had minimal GFP+ beMφ engraftment and had effectively repopulated the CNS with endogenous microglia with minimal beMφ engraftment, consistent with previously published data (Elmore et al., 2014). However, mice that had received whole body irradiation demonstrated robust engraftment of GFP+ beMφ, mimicking the synergistic effects of inducible deletion of Csf1r and whole body irradiation with BMT in our previous experiments. Due to the robust level of engraftment in this model, we sorted GFP+ beMφ from whole body irradiated mice and GFP microglia from head covered mice for RNA-seq. Mice were injected i.p. with saline or LPS 6 hours prior to cell collection. Microglia and beMφ were FACS sorted from mice with or without head-covering, respectively, and then RNA-seq followed by differential expression analysis was performed (n=3 microglia samples, pooled from 3 total mice for each sample, and n=3 beMφ samples, pooled from 3 total mice for each sample; performed once). We again found that cell type accounted for the large majority of transcriptional variance (92%) (FIG. 3C), and that when compared to microglia, beMφ had 829 differentially upregulated and 1275 differentially downregulated genes.

Example 5—beMφ are Functionally Distinct from Microglia

In order to assess beMφ function in each of the three engraftment models as discussed above, we used gene set variation analysis (GSVA) (Hanzelmann et al., 2013) to identify commonly enriched GO Biological Process (GOBP) terms in beMφ versus microglia, and vice versa. There were 117 GOBP terms commonly enriched in all three beMφ datasets, and 47 GOBP terms commonly enriched in all three microglia datasets. Within these commonly enriched functional terms, several notable functions and themes were apparent. Consistently, beMφ were enriched for "regulation of wound healing, spreading of epidermal cells," as well as multiple functions for extracellular uptake, growth factor signaling and production, extracellular matrix interaction and migration, regulation of vasculogenesis, interactions with neurons and glia, lipid metabolism, and a large number of immunologic processes. Microglia also demonstrated common functions for interaction with neurons and glia and lipid metabolism, but also notably had multiple functions related to neurotransmitters and steroids. These results suggest that while beMφ and microglia may have some similar functional themes, they are not functionally interchangeable cell types, suggesting that these are two distinct populations of CNS macrophages.

While our RNA-seq analysis suggested that microglia and beMφ are unique cell types, we decided to experimentally confirm differential response to stimuli. Using our system of BMT and PLX5622 treatment for beMφ engraftment, which allows substantial repopulation of microglia by beMφ, we first tested response to laser burn injury in live multi-photon imaging. Our results demonstrate that beMφ moved towards the laser burn faster than microglia. We then assessed response to in vivo LPS injection. Mice were given intraperitoneal LPS or saline injection, and the brains were collected for analysis 6 hours later. Sholl analysis of Iba1 staining revealed that beMφ were less ramified than microglia and demonstrated no change in ramification after LPS, whereas microglia were significantly more ramified and demonstrated significant reduction in ramification after LPS. PCA of the corresponding RNA-seq dataset demonstrated distinct clustering of samples by cell type and treatment. Differential expression analysis revealed a very large number of differentially expressed genes; 3627 upregulated and 4910 downregulated genes in beMφ as compared to microglia.

Example 6—beMφ Genetic Signature

Figure 4:
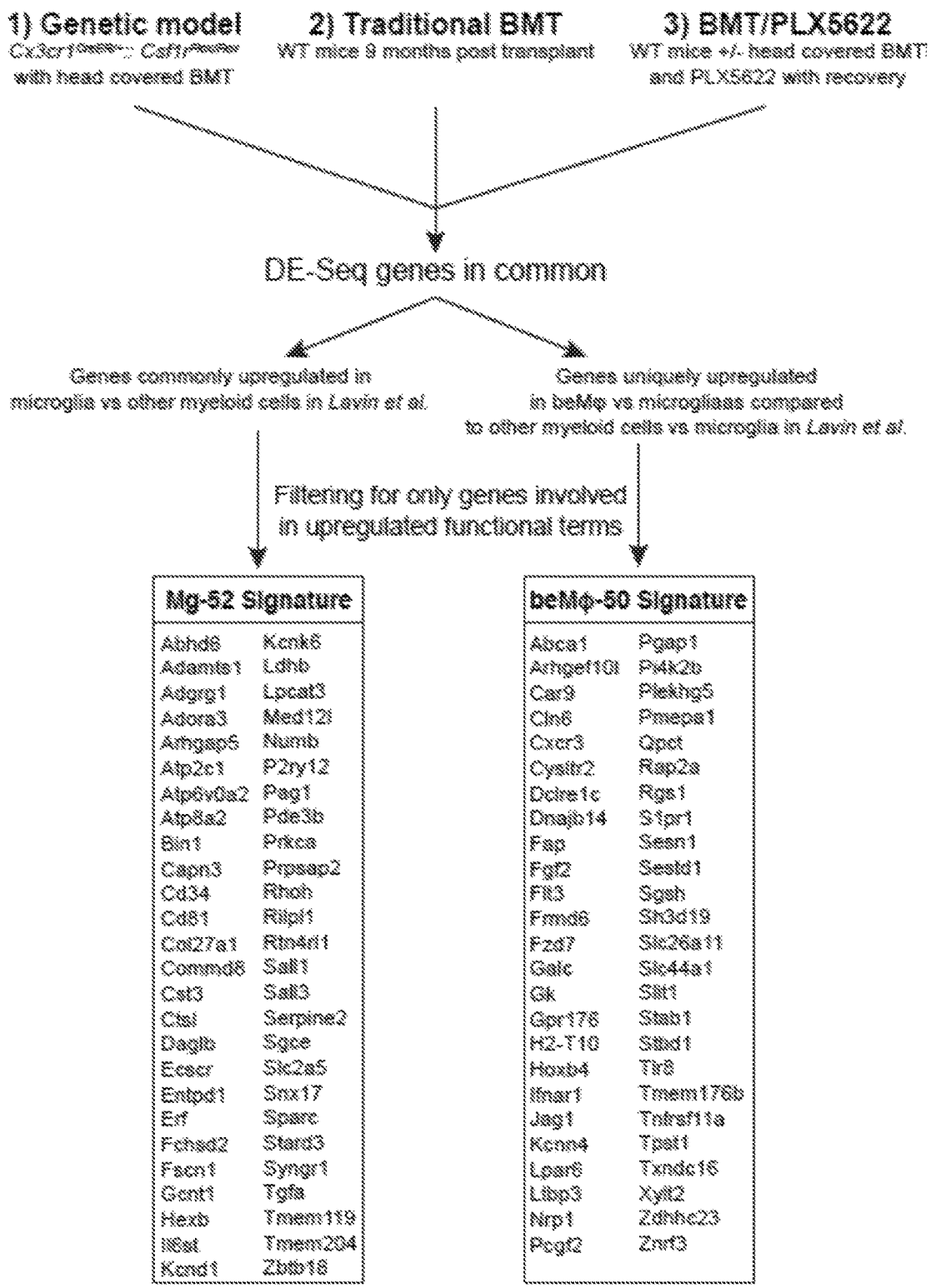
FIG. 4. Schematic showing how the Mg-52 and beMφ-50 signatures were generated by intersecting differentially expressed genes between beMφ and microglia (fold change>1.5 and adjusted p-value<0.05) from the $Cx3cr1^{CreER/+}::Csf1r^{Flox/Flox}$ model with head covered BMT and tamoxifen treatment, traditional BMT, and BMT/PLX5622 RNA-seq datasets in this study, and the myeloid cells in Lavin et al.

In our RNA-seq analysis of saline or LPS treated beMφ and microglia, we noted gene clusters that remained consistently differentially expressed between beMφ and microglia regardless of treatment, suggesting that there are core genetic signatures which may be used to define and identify beMφ versus microglia. To this end, we generated genetic signatures for beMφ and microglia by first taking the commonly upregulated genes among all three of the models of beMφ engraftment. For the beMφ signature, we then refined it by eliminating genes that were differentially expressed between peripheral myeloid cells and microglia in an RNA-seq study performed by Lavin et al. (Lavin et al., 2014); the goal of this refinement was to include only core genes that define beMφ versus microglia, and not other myeloid cells versus microglia. For the microglia signature, we refined the signature using the study by Lavin et al. (Lavin et al., 2014) by only including genes that were commonly unique to microglia in their study and to the microglia in our datasets. Finally, both signatures were refined by eliminating all genes that were not included in functionally enriched terms, thereby creating "functional" genetic signatures. This process created a 52-gene microglia signature (Mg-52; FIG. 4, Table 1) and a 50-gene beMφ signature (beMφ-50; FIG. 4, Table 2).

TABLE 1

List of genes in the Mg-52 signature

| Symbol | Ensembl | Entrez | Name |
| --- | --- | --- | --- |
| Abhd6 | ENSMUSG00000025277 | 66082 | Abhydrolase domain containing 6 |
| Adamts1 | ENSMUSG00000022893 | 11504 | A disintegrin-like and metallopeptidase (reprolysin type) with thrombospondin type 1 motif, 1 |
| Adgrg1 | ENSMUSG00000031785 | 14766 | Adhesion G protein-coupled receptor G1 |
| Adora3 | ENSMUSG00000000562 | 11542 | Adenosine A3 receptor |
| Arhgap5 | ENSMUSG00000035133 | 11855 | Rho GTPase activating protein 5 |
| Atp2c1 | ENSMUSG00000032570 | 235574 | ATPase, Ca++-sequestering |
| Atp6v0a2 | ENSMUSG00000038023 | 21871 | ATPase, H+ transporting, lysosomal V0 subunit A2 |
| Atp8a2 | ENSMUSG00000021983 | 50769 | ATPase, aminophospholipid transporter-like, class I, type 8A, member 2 |
| Bin1 | ENSMUSG00000024381 | 30948 | Bridging integrator 1 |
| Capn3 | ENSMUSG00000079110 | 12335 | Calpain 3 |
| Cd34 | ENSMUSG00000016494 | 12490 | CD34 antigen |
| Cd81 | ENSMUSG00000037706 | 12520 | CD81 antigen |
| Col27a1 | ENSMUSG00000045672 | 373864 | Collagen, type XXVII, alpha 1 |
| Commd8 | ENSMUSG00000029213 | 27784 | COMM domain containing 8 |
| Cst3 | ENSMUSG00000027447 | 13010 | Cystatin C |

TABLE 1-continued

List of genes in the Mg-52 signature

| Symbol | Ensembl | Entrez | Name |
|---|---|---|---|
| Ctsl | ENSMUSG00000021477 | 13039 | Cathepsin L |
| Daglb | ENSMUSG00000039206 | 231871 | Diacylglycerol lipase, beta |
| Ecscr | ENSMUSG00000073599 | 68545 | Endothelial cell surface expressed chemotaxis and apoptosis regulator |
| Entpd1 | ENSMUSG00000048120 | 12495 | Ectonucleoside triphosphate diphosphohydrolase 1 |
| Erf | ENSMUSG00000040857 | 13875 | Ets2 repressor factor |
| Fchsd2 | ENSMUSG00000030691 | 207278 | FCH and double SH3 domains 2 |
| Fscn1 | ENSMUSG00000029581 | 14086 | Fascin actin-bundling protein 1 |
| Gcnt1 | ENSMUSG00000038843 | 14537 | Glucosaminyl (N-acetyl) transferase 1, core 2 |
| Hexb | ENSMUSG00000021665 | 15212 | Hexosaminidase B |
| Il6st | ENSMUSG00000021756 | 16195 | Interleukin 6 signal transducer |
| Kcnd1 | ENSMUSG00000009731 | 16506 | Potassium voltage-gated channel, Shal-related family, member 1 |
| Kcnk6 | ENSMUSG00000046410 | 52150 | Potassium inwardly-rectifying channel, subfamily K, member 6 |
| Ldhb | ENSMUSG00000030246 | 16832 | Lactate dehydrogenase B |
| Lpcat3 | ENSMUSG00000004270 | 14792 | Lysophosphatidylcholine acyltransferase 3 |
| Med12l | ENSMUSG00000056476 | 329650 | Mediator complex subunit 12-like |
| Numb | ENSMUSG00000021224 | 18222 | Numb homolog (Drosophila) |
| P2ry12 | ENSMUSG00000036353 | 70839 | Purinergic receptor P2Y, G-protein coupled 12 |
| Pag1 | ENSMUSG00000027508 | 94212 | Phosphoprotein associated with glycosphingolipid microdomains 1 |
| Pde3b | ENSMUSG00000030671 | 18576 | Phosphodiesterase 3B, cGMP-inhibited |
| Prkca | ENSMUSG00000050965 | 18750 | Protein kinase C, alpha |
| Prpsap2 | ENSMUSG00000020528 | 212627 | Phosphoribosyl pyrophosphate synthetase-associated protein 2 |
| Rhoh | ENSMUSG00000029204 | 74734 | Ras homolog family member H |
| Rilpl1 | ENSMUSG00000029392 | 75695 | Rab interacting lysosomal protein-like 1 |
| Rtn4rl1 | ENSMUSG00000045287 | 237847 | Reticulon 4 receptor-like 1 |
| Sall1 | ENSMUSG00000031665 | 58198 | Sal-like 1 (Drosophila) |
| Sall3 | ENSMUSG00000024565 | 20689 | Sal-like 3 (Drosophila) |
| Serpine2 | ENSMUSG00000026249 | 20720 | Serine (or cysteine) peptidase inhibitor, clade E, member 2 |
| Sgce | ENSMUSG00000004631 | 20392 | Sarcoglycan, epsilon |
| Slc2a5 | ENSMUSG00000028976 | 56485 | Solute carrier family 2 (facilitated glucose transporter), member 5 |
| Snx17 | ENSMUSG00000029146 | 266781 | Sorting nexin 17 |
| Sparc | ENSMUSG00000018593 | 20692 | Secreted acidic cysteine rich glycoprotein |
| Stard3 | ENSMUSG00000018167 | 59045 | START domain containing 3 |
| Syngr1 | ENSMUSG00000022415 | 20972 | Synaptogyrin 1 |
| Tgfa | ENSMUSG00000029999 | 21802 | Transforming growth factor alpha |
| Tmem119 | ENSMUSG00000054675 | 231633 | Transmembrane protein 119 |
| Tmem204 | ENSMUSG00000024168 | 407831 | Transmembrane protein 204 |
| Zbtb18 | ENSMUSG00000063659 | 30928 | Zinc finger and BTB domain containing 18 |

TABLE 2

List of genes in the beMφ-50 signature

| Symbol | Ensembl | Entrez | Name |
|---|---|---|---|
| Abca1 | ENSMUSG00000015243 | 11303 | ATP-binding cassette, sub-family A (ABC1), member 1 |
| Arhgef10l | ENSMUSG00000040964 | 72754 | Rho guanine nucleotide exchange factor (GEF) 10-like |
| Car9 | ENSMUSG00000028463 | 230099 | Carbonic anhydrase 9 |
| Cln6 | ENSMUSG00000032245 | 76524 | Ceroid-lipofuscinosis, neuronal 6 |
| Cxcr3 | ENSMUSG00000050232 | 12766 | Chemokine (C-X-C motif) receptor 3 |
| Cysltr2 | ENSMUSG00000033470 | 70086 | Cysteinyl leukotriene receptor 2 |
| Dclre1c | ENSMUSG00000026648 | 227525 | DNA cross-link repair 1C |
| Dnajb14 | ENSMUSG00000074212 | 70604 | DnaJ heat shock protein family (Hsp40) member B14 |
| Fap | ENSMUSG00000000392 | 14089 | Fibroblast activation protein |
| Fgf2 | ENSMUSG00000037225 | 14173 | Fibroblast growth factor 2 |
| Flt3 | ENSMUSG00000042817 | 14255 | FMS-like tyrosine kinase 3 |
| Frmd6 | ENSMUSG00000048285 | 319710 | FERM domain containing 6 |
| Fzd7 | ENSMUSG00000041075 | 14369 | Frizzled class receptor 7 |
| Galc | ENSMUSG00000021003 | 14420 | Galactosylceramidase |
| Gk | ENSMUSG00000025059 | 14933 | Glycerol kinase |
| Gpr176 | ENSMUSG00000040133 | 381413 | G protein-coupled receptor 176 |
| H2-T10 | ENSMUSG00000079491 | 15024 | Histocompatibility 2, T region locus 10 |

TABLE 2-continued

List of genes in the beMφ-50 signature

| Symbol | Ensembl | Entrez | Name |
|---|---|---|---|
| Hoxb4 | ENSMUSG00000038692 | 15412 | Homeobox B4 |
| Ifnar1 | ENSMUSG00000022967 | 15975 | Interferon (alpha and beta) receptor 1 |
| Jag1 | ENSMUSG00000027276 | 16449 | Jagged 1 |
| Kcnn4 | ENSMUSG00000054342 | 16534 | Potassium intermediate/small conductance calcium-activated channel, subfamily N, member 4 |
| Lpar6 | ENSMUSG00000033446 | 67168 | Lysophosphatidic acid receptor 6 |
| Ltbp3 | ENSMUSG00000024940 | 16998 | Latent transforming growth factor beta binding protein 3 |
| Nrp1 | ENSMUSG00000025810 | 18186 | Neuropilin 1 |
| Pcgf2 | ENSMUSG00000018537 | 22658 | Polycomb group ring finger 2 |
| Pgap1 | ENSMUSG00000073678 | 241062 | Post-GPI attachment to proteins 1 |
| Pi4k2b | ENSMUSG00000029186 | 67073 | Phosphatidylinositol 4-kinase type 2 beta |
| Plekhg5 | ENSMUSG00000039713 | 269608 | Pleckstrin homology domain containing, family G (with RhoGef domain) member 5 |
| Pmepa1 | ENSMUSG00000038400 | 65112 | Prostate transmembrane protein, androgen induced 1 |
| Qpct | ENSMUSG00000024084 | 70536 | Glutaminyl-peptide cyclotransferase (glutaminyl cyclase) |
| Rap2a | ENSMUSG00000051615 | 76108 | RAS related protein 2a |
| Rgs1 | ENSMUSG00000026358 | 50778 | Regulator of G-protein signaling 1 |
| S1pr1 | ENSMUSG00000045092 | 13609 | Sphingosine-1-phosphate receptor 1 |
| Sesn1 | ENSMUSG00000038332 | 140742 | Sestrin 1 |
| Sestd1 | ENSMUSG00000042272 | 228071 | SEC14 and spectrin domains 1 |
| Sgsh | ENSMUSG00000005043 | 27029 | N-sulfoglucosamine sulfohydrolase (sulfamidase) |
| Sh3d19 | ENSMUSG00000028082 | 27059 | SH3 domain protein D19 |
| Slc26a11 | ENSMUSG00000039908 | 268512 | Solute carrier family 26, member 11 |
| Slc44a1 | ENSMUSG00000028412 | 100434 | Solute carrier family 44, member 1 |
| Slit1 | ENSMUSG00000025020 | 20562 | Slit homolog 1 (Drosophila) |
| Stab1 | ENSMUSG00000042286 | 192187 | Stabilin 1 |
| Stbd1 | ENSMUSG00000047963 | 52331 | Starch binding domain 1 |
| Tlr8 | ENSMUSG00000040522 | 170744 | Toll-like receptor 8 |
| Tmem176b | ENSMUSG00000029810 | 65963 | Transmembrane protein 176B |
| Tnfrsf11a | ENSMUSG00000026321 | 21934 | Tumor necrosis factor receptor superfamily, member 11a, NFKB activator |
| Tpst1 | ENSMUSG00000034118 | 22021 | Protein-tyrosine sulfotransferase 1 |
| Txndc16 | ENSMUSG00000021830 | 70561 | Thioredoxin domain containing 16 |
| Xylt2 | ENSMUSG00000020868 | 217119 | Xylosyltransferase II |
| Zdhhc23 | ENSMUSG00000036304 | 332175 | Zinc finger, DHHC domain containing 23 |
| Znrf3 | ENSMUSG00000041961 | 407821 | Zinc and ring finger 3 |

Of note, several previously identified microglia-specific genes were included in the Mg-52 signature, such as Cst3, Hexb, P2ry12, and Sall1, and Tmem119. Based on this, we tested P2ry12 as a marker of microglia versus beMφ. Indeed, while both beMφ and microglia stained for Iba1, P2ry12 was a unique marker for microglia.

Figure 5:
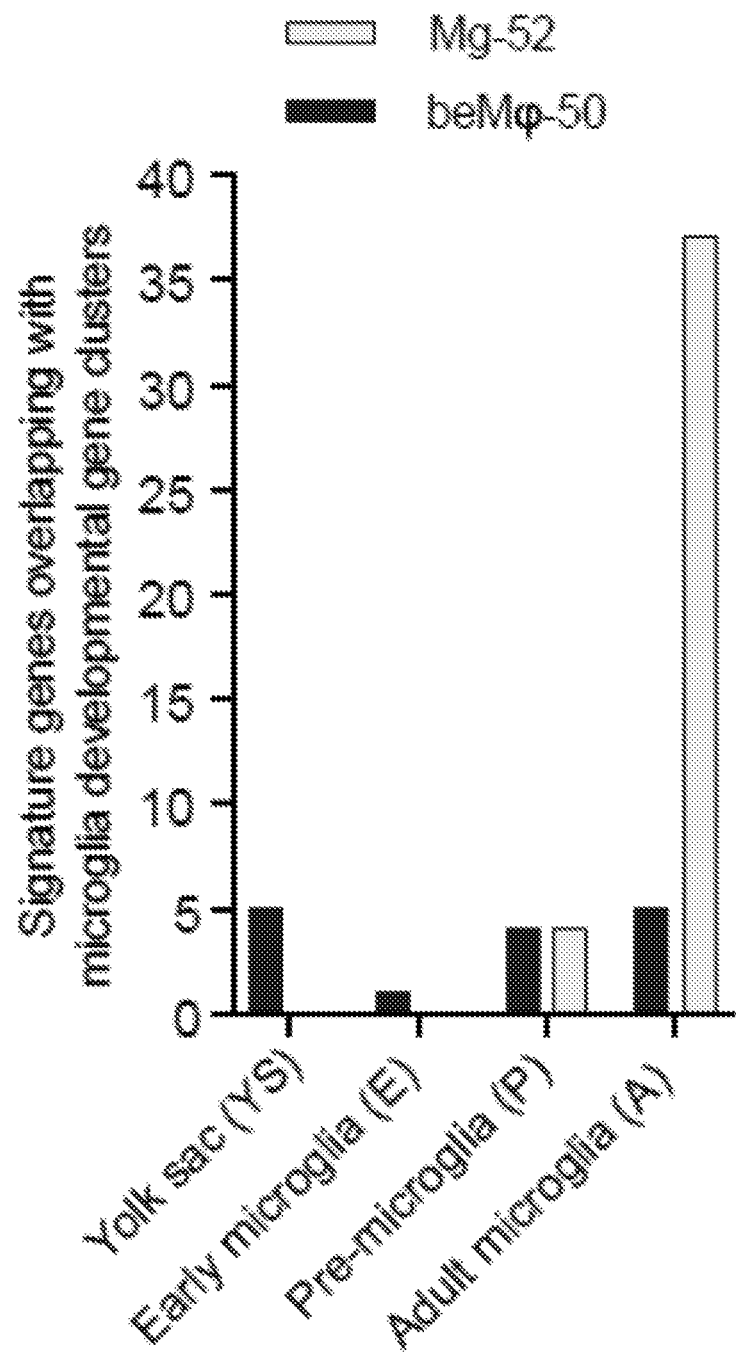
FIG. 5. Overlap of the Mg-52 and beMφ-50 in the microglia developmental stages from Matcovitch-Natan et al.

We next evaluated the reliability of our signatures within the datasets used to generate them. As expected, all three datasets universally demonstrated enrichment of Mg-52 in microglia, and enrichment of the beMφ-50 in beMφ. In a study by Matcovitch-Natan et al. (Matcovitch-Natan et al., 2016), gene clusters involved in stages of microglia development were identified. We assessed the overlap of our signatures with these microglia developmental gene clusters, and found that the only substantial overlap occurred with the Mg-52 signature and the "Adult Microglia" developmental gene cluster (37/52 genes in Mg-52; FIG. 5). These results supported the idea that the Mg-52 signature is specific to adult microglia, and that the beMφ-50 signature does not correlate to any microglia developmental programs.

To test the specificity of Mg-52 and beMφ-50 for their respective cell types, we used a competitive gene set test (CAMERA) (Wu and Smyth, 2012). Publicly available transcriptomic datasets of immune cells (Heng et al., 2008), neurons (Srinivasan et al., 2016), astrocytes (Srinivasan et al., 2016), beMφ (Bruttger et al., 2015), and our LPS-treated beMφ data (which was not used in the generation of signatures) were used to validate the signatures. All of these datasets contain microglia samples that were used as a common reference cell in our CAMERA analysis. As expected, neither neurons nor astrocytes were enriched for beMφ-50, but microglia were enriched for the Mg-52 signature as compared to neurons and astrocytes. Similarly, LPS-treated microglia were not enriched for beMφ-50 as compared to control microglia, while control microglia were enriched for Mg-52.

Likewise, the Mg-52 signature was enriched in microglia compared to all immune cell types tested from the publically available Immgen microarray dataset (Heng et al., 2008), again supporting the fidelity of this signature for the detection of microglia vs. non-microglia. However, three peripheral immune cell types were significantly enriched for beMφ-50; small intestine serosal macrophages, lung CD11b+ macrophages, and small intestine lamina propria macrophages. Interestingly, all three of these are monocyte-derived macrophages, providing further evidence of a monocyte origin for beMφ.

Importantly, there was strong enrichment for beMφ-50 in beMφ transcriptomes generated in another laboratory (Bruttger et al., 2015). We also observed strong enrichment for beMφ-50 in LPS-treated beMφ, confirming our initial observation that beMφ and microglia have core genes that can be used to define each cell type regardless of a strong stimulus.

Finally, we used our signatures to interrogate recently published data that purports to have generated iPSC-derived microglia-like cells (Takata et al., 2017). When CAMERA analysis on RNA-seq data from iPSC-derived microglia-like cells (iMac) versus bone marrow-derived macrophages (BM Mac) over the course of an in vitro co-culture with neurons, we found that Mg-52 became significantly enriched in iMac by day 3 of co-culture, and remained enriched through day 12. By comparison, beMϕ-50 was enriched in BM Mac on days 0 and 12. These results supported the conclusions of Takata et al. (Takata et al., 2017) that they had generated microglia-like cells in vitro.

Overall, these data confirmed that Mg-52 and beMϕ-50 represent core signatures that may be used to define and identify microglia and beMφ in a direct comparison. In addition, the fact that each cell type has a distinct core genetic program lends strong evidence that beMφ indeed represent an independent type of macrophage that could have a long-lived presence and unique functional implications in the CNS.

REFERENCES

Acton, S. T. 2001. Fast Algorithms for Area Morphology. *Digital Signal Processing* 11:187-203.

Acton, S. T., and D. P. Mukherjee. 2000. Area operators for edge detection. *Pattern Recognition Letters* 21:771-777.

Ajami, B., J. L. Bennett, C. Krieger, W. Tetzlaff, and F. M. Rossi. 2007. Local self-renewal can sustain CNS microglia maintenance and function throughout adult life. *Nature neuroscience* 10:1538-1543.

Alliot, F., I. Godin, and B. Pessac. 1999. Microglia derive from progenitors, originating from the yolk sac, and which proliferate in the brain. *Brain Res Dev Brain Res* 117:145-152.

Anders, S., P. T. Pyl, and W. Huber. 2015. HTSeq—a Python framework to work with high-throughput sequencing data. *Bioinformatics* 31:166-169.

Andrews, S. 2010. FastQC: a quality control tool for high throughput sequence data. In.

Ashburner, M., C. A. Ball, J. A. Blake, D. Botstein, H. Butler, J. M. Cherry, A. P. Davis, K. Dolinski, S. S. Dwight, J. T. Eppig, M. A. Harris, D. P. Hill, L. Issel-Tarver, A. Kasarskis, S. Lewis, J. C. Matese, J. E. Richardson, M. Ringwald, G. M. Rubin, and G. Sherlock. 2000. Gene ontology: tool for the unification of biology. The Gene Ontology Consortium. *Nature genetics* 25:25-29.

Beattie, L., A. Sawtell, J. Mann, T. C. Frame, B. Teal, F. de Labastida Rivera, N. Brown, K. Walwyn-Brown, J. W. Moore, S. MacDonald, E. K. Lim, J. E. Dalton, C. R. Engwerda, K. P. MacDonald, and P. M. Kaye. 2016. Bone marrow-derived and resident liver macrophages display unique transcriptomic signatures but similar biological functions. *Journal of hepatology* 65:758-768.

Bolger, A. M., M. Lohse, and B. Usadel. 2014. Trimmomatic: a flexible trimmer for Illumina sequence data. *Bioinformatics* 30:2114-2120.0

Bosco, N., L. K. Swee, A. Benard, R. Ceredig, and A. Rolink. 2010. Auto-reconstitution of the T-cell compartment by radioresistant hematopoietic cells following lethal irradiation and bone marrow transplantation. *Exp Hematol* 38:222-232 e222.

Bruttger, J., K. Karram, S. Wortge, T. Regen, F. Marini, N. Hoppmann, M. Klein, T. Blank, S. Yona, Y. Wolf, M. Mack, E. Pinteaux, W. Muller, F. Zipp, H. Binder, T. Bopp, M. Prinz, S. Jung, and A. Waisman. 2015. Genetic Cell Ablation Reveals Clusters of Local Self-Renewing Microglia in the Mammalian Central Nervous System. *Immunity* 43:92-106.

Butovsky, O., M. Koronyo-Hamaoui, G. Kunis, E. Ophir, G. Landa, H. Cohen, and M. Schwartz. 2006. Glatiramer acetate Fights against Alzheimer's disease by inducing dendritic-like microglia expressing insulin-like growth factor 1. *Proceedings of the National Academy of Sciences of the United States of America* 103:11784-11789.

Butovsky, O., G. Kunis, M. Koronyo-Hamaoui, and M. Schwartz. 2007. Selective ablation of bone marrow-derived dendritic cells increases amyloid plaques in a mouse Alzheimer's disease model. *The European journal of neuroscience* 26:413-416.

Butovsky, O., S. Siddiqui, G. Gabriely, A. J. Lanser, B. Dake, G. Murugaiyan, C. E. Doykan, P. M. Wu, R. R. Gali, L. K. Iyer, R. Lawson, J. Berry, A. M. Krichevsky, M. E. Cudkowicz, and H. L. Weiner. 2012. Modulating inflammatory monocytes with a unique microRNA gene signature ameliorates murine ALS. *The Journal of clinical investigation* 122:3063-3087.

Carvalho, B. S., and R. A. Irizarry. 2010. A framework for oligonucleotide microarray preprocessing. *Bioinformatics* 26:2363-2367.

Chen, S. K., P. Tvrdik, E. Peden, S. Cho, S. Wu, G. Spangrude, and M. R. Capecchi. 2010. Hematopoietic origin of pathological grooming in Hoxb8 mutant mice. *Cell* 141:775-785.

Chiu, I. M., E. T. Morimoto, H. Goodarzi, J. T. Liao, S. O'Keeffe, H. P. Phatnani, M. Muratet, M. C. Carroll, S. Levy, S. Tavazoie, R. M. Myers, and T. Maniatis. 2013. A neurodegeneration-specific gene-expression signature of acutely isolated microglia from an amyotrophic lateral sclerosis mouse model. Cell Rep 4:385-401.

Cronk, J. C., N.C. Derecki, E. Ji, Y. Xu, A. E. Lampano, I. Smirnov, W. Baker, G. T. Norris, I. Marin, N. Coddington, Y. Wolf, S. D. Turner, A. Aderem, A. L. Klibanov, T. H. Harris, S. Jung, V. Litvak, and J. Kipnis. 2015. Methyl-CpG Binding Protein 2 Regulates Microglia and Macrophage Gene Expression in Response to Inflammatory Stimuli. *Immunity* 42:679-691.

Davalos, D., J. Grutzendler, G. Yang, J. V. Kim, Y. Zuo, S. Jung, D. R. Littman, M. L. Dustin, and W. B. Gan. 2005. ATP mediates rapid microglial response to local brain injury in vivo. *Nature neuroscience* 8:752-758.

Derecki, N.C., J. C. Cronk, Z. Lu, E. Xu, S. B. Abbott, P. G. Guyenet, and J. Kipnis. 2012. Wild-type microglia arrest pathology in a mouse model of Rett syndrome. *Nature* 484:105-109.

Dobin, A., C. A. Davis, F. Schlesinger, J. Drenkow, C. Zaleski, S. Jha, P. Batut, M. Chaisson, and T. R. Gingeras. 2013. STAR: ultrafast universal RNA-seq aligner. *Bioinformatics* 29:15-21.

Elmore, M. R., A. R. Najafi, M. A. Koike, N. N. Dagher, E. E. Spangenberg, R. A. Rice, M. Kitazawa, B. Matusow, H. Nguyen, B. L. West, and K. N. Green. 2014. Colony-stimulating factor 1 receptor signaling is necessary for microglia viability, unmasking a microglia progenitor cell in the adult brain. *Neuron* 82:380-397.

Epelman, S., K. J. Lavine, A. E. Beaudin, D. K. Sojka, J. A. Carrero, B. Calderon, T. Brija, E. L. Gautier, S. Ivanov, A. T. Satpathy, J. D. Schilling, R. Schwendener, I. Sergin, B. Razani, E. C. Forsberg, W. M. Yokoyama, E. R. Unanue, M. Colonna, G. J. Randolph, and D. L. Mann. 2014. Embryonic and adult-derived resident cardiac macrophages are maintained through distinct mechanisms at steady state and during inflammation. *Immunity* 40:91-104.

Filiano, A. J., Y. Xu, N. J. Tustison, R. L. Marsh, W. Baker, I. Smirnov, C. C. Overall, S. P. Gadani, S. D. Turner, Z. Weng, S. N. Peerzade, H. Chen, K. S. Lee, M. M. Scott, M. P. Beenhakker, V. Litvak, and J. Kipnis. 2016. Unexpected role of interferon-gamma in regulating neuronal connectivity and social behaviour. *Nature* 535:425-429.

Gautier, L., L. Cope, B. M. Bolstad, and R. A. Irizarry. 2004. affy—analysis of Affymetrix GeneChip data at the probe level. *Bioinformatics* 20:307-315.

Gehlenborg, N. 2016. UpSetR: A More Scalable Alternative to Venn and Euler Diagrams for Visualizing Intersecting Sets. R package version 1.2.2. In.

Gibbings, S. L., R. Goyal, A. N. Desch, S. M. Leach, M. Prabagar, S. M. Atif, D. L. Bratton, W. Janssen, and C. V. Jakubzick. 2015. Transcriptome analysis highlights the conserved difference between embryonic and postnatal-derived alveolar macrophages. *Blood* 126:1357-1366.

Ginhoux, F., and M. Merad. 2011. [Microglia arise from extra-embryonic yolk sac primitive progenitors]. *Med Sci (Paris)* 27:719-724.

Goldmann, T., P. Wieghofer, P. F. Muller, Y. Wolf, D. Varol, S. Yona, S. M. Brendecke, K. Kierdorf, O. Staszewski, M. Datta, T. Luedde, M. Heikenwalder, S. Jung, and M. Prinz. 2013. A new type of microglia gene targeting shows TAK1 to be pivotal in CNS autoimmune inflammation. *Nature neuroscience* 16:1618-1626.

Hanzelmann, S., R. Castelo, and J. Guinney. 2013. GSVA: gene set variation analysis for microarray and RNA-seq data. *BMC bioinformatics* 14:7.

Harrow, J., A. Frankish, J. M. Gonzalez, E. Tapanari, M. Diekhans, F. Kokocinski, B. L. Aken, D. Barrell, A. Zadissa, S. Searle, I. Barnes, A. Bignell, V. Boychenko, T. Hunt, M. Kay, G. Mukherjee, J. Rajan, G. Despacio-Reyes, G. Saunders, C. Steward, R. Harte, M. Lin, C. Howald, A. Tanzer, T. Derrien, J. Chrast, N. Walters, S. Balasubramanian, B. Pei, M. Tress, J. M. Rodriguez, I. Ezkurdia, J. van Baren, M. Brent, D. Haussler, M. Kellis, A. Valencia, A. Reymond, M. Gerstein, R. Guigo, and T. J. Hubbard. 2012. GENCODE: the reference human genome annotation for The ENCODE Project. *Genome research* 22:1760-1774.

Heng, T. S., M. W. Painter, and C. Immunological Genome Project. 2008. The Immunological Genome Project: networks of gene expression in immune cells. *Nat Immunol* 9:1091-1094.

Hoeffel, G., J. Chen, Y. Lavin, D. Low, F. F. Almeida, P. See, A. E. Beaudin, J. Lum, I. Low, E. C. Forsberg, M. Poidinger, F. Zolezzi, A. Larbi, L. G. Ng, J. K. Chan, M. Greter, B. Becher, I. M. Samokhvalov, M. Merad, and F. Ginhoux. 2015. C-Myb(+) erythro-myeloid progenitor-derived fetal monocytes give rise to adult tissue-resident macrophages. *Immunity* 42:665-678.

Hsiao, E. Y., S. W. McBride, J. Chow, S. K. Mazmanian, and P. H. Patterson. 2012. Modeling an autism risk factor in mice leads to permanent immune dysregulation. *Proceedings of the National Academy of Sciences of the United States of America* 109:12776-12781.

Huang, Y., Z. Xu, S. Xiong, F. Sun, G. Qin, G. Hu, J. Wang, L. Zhao, Y. X. Liang, T. Wu, Z. Lu, M. S. Humayun, K. F. So, Y. Pan, N. Li, T. F. Yuan, Y. Rao, and B. Peng. 2018. Repopulated microglia are solely derived from the proliferation of residual microglia after acute depletion. *Nature neuroscience*

Irizarry, R. A., B. M. Bolstad, F. Collin, L. M. Cope, B. Hobbs, and T. P. Speed. 2003. Summaries of Affymetrix GeneChip probe level data. *Nucleic acids research* 31:e15.

Jay, T. R., C. M. Miller, P. J. Cheng, L. C. Graham, S. Bemiller, M. L. Broihier, G. Xu, D. Margevicius, J. C. Karlo, G. L. Sousa, A. C. Cotleur, O. Butovsky, L. Bekris, S. M. Staugaitis, J. B. Leverenz, S. W. Pimplikar, G. E. Landreth, G. R. Howell, R. M. Ransohoff, and B. T. Lamb. 2015. TREM2 deficiency eliminates TREM2+ inflammatory macrophages and ameliorates pathology in Alzheimer's disease mouse models. *The Journal of experimental medicine* 212:287-295.

Jung, S., and M. Schwartz. 2012. Non-identical twins—microglia and monocyte-derived macrophages in acute injury and autoimmune inflammation. *Front Immunol* 3:89.

Kolde, R. 2015. Pretty Heatmaps. R package version 1.0.8.

Krivit, W., C. Peters, and E. G. Shapiro. 1999. Bone marrow transplantation as effective treatment of central nervous system disease in globoid cell leukodystrophy, metachromatic leukodystrophy, adrenoleukodystrophy, mannosidosis, fucosidosis, aspartylglucosaminuria, Hurler, Maroteaux-Lamy, and Sly syndromes, and Gaucher disease type III. *Curr Opin Neurol* 12:167-176.

Krivit, W., J. H. Sung, E. G. Shapiro, and L. A. Lockman. 1995. Microglia: the effector cell for reconstitution of the central nervous system following bone marrow transplantation for lysosomal and peroxisomal storage diseases. *Cell Transplant* 4:385-392.

Larochelle, A., M. A. Bellavance, J. P. Michaud, and S. Rivest. 2016. Bone marrow-derived macrophages and the CNS: An update on the use of experimental chimeric mouse models and bone marrow transplantation in neurological disorders. *Biochimica et biophysica acta* 1862:310-322.

Lassmann, T., Y. Hayashizaki, and C. O. Daub. 2011. SAMStat: monitoring biases in next generation sequencing data. *Bioinformatics* 27:130-131.

Lavin, Y., D. Winter, R. Blecher-Gonen, E. David, H. Keren-Shaul, M. Merad, S. Jung, and I. Amit. 2014. Tissue-resident macrophage enhancer landscapes are shaped by the local microenvironment. *Cell* 159:1312-1326.

Law, C. W., Y. Chen, W. Shi, and G. K. Smyth. 2014. voom: Precision weights unlock linear model analysis tools for RNA-seq read counts. *Genome biology* 15:R29.

Leek, J. T., W. E. Johnson, H. S. Parker, A. E. Jaffe, and J. D. Storey. 2012. The sva package for removing batch effects and other unwanted variation in high-throughput experiments. *Bioinformatics* 28:882-883.

Leek, J. T., and J. D. Storey. 2007. Capturing heterogeneity in gene expression studies by surrogate variable analysis. *PLoS genetics* 3:1724-1735.

Lex, A., N. Gehlenborg, H. Strobelt, R. Vuillemot, and H. Pfister. 2014. UpSet: Visualization of Intersecting Sets. *IEEE transactions on visualization and computer graphics* 20:1983-1992.

Li, H., B. Handsaker, A. Wysoker, T. Fennell, J. Ruan, N. Homer, G. Marth, G. Abecasis, R. Durbin, and S. Genome Project Data Processing. 2009. The Sequence Alignment/Map format and SAMtools. *Bioinformatics* 25:2078-2079.

Li, J., K. Chen, L. Zhu, and J. W. Pollard. 2006. Conditional deletion of the colony stimulating factor-1 receptor (c-fms proto-oncogene) in mice. *Genesis* 44:328-335.

Love, M. I., W. Huber, and S. Anders. 2014. Moderated estimation of fold change and dispersion for RNA-seq data with DESeq2. *Genome biology* 15:550.

Lu, Z., M. R. Elliott, Y. Chen, J. T. Walsh, A. L. Klibanov, K. S. Ravichandran, and J. Kipnis. 2011. Phagocytic activity of neuronal progenitors regulates adult neurogenesis. *Nature cell biology* 13:1076-1083.

Matcovitch-Natan, O., D. R. Winter, A. Giladi, S. Vargas Aguilar, A. Spinrad, S. Sarrazin, H. Ben-Yehuda, E. David, F. Zelada Gonzalez, P. Perrin, H. Keren-Shaul, M. Gury, D. Lara-Astaiso, C. A. Thaiss, M. Cohen, K. Bahar Halpern, K. Baruch, A. Deczkowska, E. Lorenzo-Vivas, S. Itzkovitz, E. Elinav, M. H. Sieweke, M. Schwartz, and I. Amit. 2016. Microglia development follows a stepwise program to regulate brain homeostasis. *Science*

Mildner, A., H. Schmidt, M. Nitsche, D. Merkler, U. K. Hanisch, M. Mack, M. Heikenwalder, W. Bruck, J. Priller, and M. Prinz. 2007. Microglia in the adult brain arise from Ly-6ChiCCR2+ monocytes only under defined host conditions. *Nature neuroscience* 10:1544-1553.

Platt, F. M., and R. H. Lachmann. 2009. Treating lysosomal storage disorders: current practice and future prospects. *Biochimica et biophysica acta* 1793:737-745.

Priller, J., A. Flugel, T. Wehner, M. Boentert, C. A. Haas, M. Prinz, F. Fernandez-Klett, K. Prass, I. Bechmann, B. A. de Boer, M. Frotscher, G. W. Kreutzberg, D. A. Persons, and U. Dirnagl. 2001. Targeting gene-modified hematopoietic cells to the central nervous system: use of green fluorescent protein uncovers microglial engraftment. *Nat Med* 7:1356-1361.

Prinz, M., and J. Priller. 2014. Microglia and brain macrophages in the molecular age: from origin to neuropsychiatric disease. Nature reviews. *Neuroscience* 15:300-312.

Radjavi, A., I. Smirnov, N. Derecki, and J. Kipnis. 2014. Dynamics of the meningeal CD4(+) T-cell repertoire are defined by the cervical lymph nodes and facilitate cognitive task performance in mice. *Molecular psychiatry* 19:531-533.

Ritchie, M. E., B. Phipson, D. Wu, Y. Hu, C. W. Law, W. Shi, and G. K. Smyth. 2015. limma powers differential expression analyses for RNA-sequencing and microarray studies. *Nucleic acids research* 43:e47.

Rolls, A., R. Shechter, A. London, Y. Segev, J. Jacob-Hirsch, N. Amariglio, G. Rechavi, and M. Schwartz. 2008. Two faces of chondroitin sulfate proteoglycan in spinal cord repair: a role in microglia/macrophage activation. *PLoS medicine* 5:e171.

Scott, C. L., F. Zheng, P. De Baetselier, L. Martens, Y. Saeys, S. De Prijck, S. Lippens, C. Abels, S. Schoonooghe, G. Raes, N. Devoogdt, B. N. Lambrecht, A. Beschin, and M. Guilliams. 2016. Bone marrow-derived monocytes give rise to self-renewing and fully differentiated Kupffer cells. *Nature communications* 7:10321.

Scott Thomas Acton, N. R. 2006. Biomedical image analysis: Tracking. Morgan & Claypool Publishers, Shechter, R., A. London, C. Varol, C. Raposo, M. Cusimano, G. Yovel, A. Rolls, M. Mack, S. Pluchino, G. Martino, S. Jung, and M. Schwartz. 2009. Infiltrating blood-derived macrophages are vital cells playing an anti-inflammatory role in recovery from spinal cord injury in mice. *PLoS medicine* 6:e1000113.

Sheng, J., C. Ruedl, and K. Karjalainen. 2015. Most Tissue-Resident Macrophages Except Microglia Are Derived from Fetal Hematopoietic Stem Cells. *Immunity* 43:382-393.

Silver, J. D., M. E. Ritchie, and G. K. Smyth. 2009. Microarray background correction: maximum likelihood estimation for the normal-exponential convolution. *Biostatistics* 10:352-363.

Srinivasan, K., B. A. Friedman, J. L. Larson, B. E. Lauffer, L. D. Goldstein, L. L. Appling, J. Borneo, C. Poon, T. Ho, F. Cai, P. Steiner, M. P. van der Brug, Z. Modrusan, J. S. Kaminker, and D. V. Hansen. 2016. Untangling the brain's neuroinflammatory and neurodegenerative transcriptional responses. *Nature communications* 7:11295.

Takata, K., T. Kozaki, C. Z. W. Lee, M. S. Thion, M. Otsuka, S. Lim, K. H. Utami, K. Fidan, D. S. Park, B. Malleret, S. Chakarov, P. See, D. Low, G. Low, M. Garcia-Miralles, R. Zeng, J. Zhang, C. C. Goh, A. Gul, S. Hubert, B. Lee, J. Chen, I. Low, N. B. Shadan, J. Lum, T. S. Wei, E. Mok, S. Kawanishi, Y. Kitamura, A. Larbi, M. Poidinger, L. Renia, L. G. Ng, Y. Wolf, S. Jung, T. Onder, E. Newell, T. Huber, E. Ashihara, S. Garel, M. A. Pouladi, and F. Ginhoux. 2017. Induced-Pluripotent-Stem-Cell-Derived Primitive Macrophages Provide a Platform for Modeling Tissue-Resident Macrophage Differentiation and Function. *Immunity* 47:183-198 e186.

The Gene Ontology, C. 2017. Expansion of the Gene Ontology knowledgebase and resources. *Nucleic acids research* 45:D331-D338.

Theriault, P., A. ElAli, and S. Rivest. 2015. The dynamics of monocytes and microglia in Alzheimer's disease. *Alzheimers Res Ther* 7:41.

van de Laar, L., W. Saelens, S. De Prijck, L. Martens, C. L. Scott, G. Van Isterdael, E. Hoffmann, R. Beyaert, Y. Saeys, B. N. Lambrecht, and M. Guilliams. 2016. Yolk Sac Macrophages, Fetal Liver, and Adult Monocytes Can Colonize an Empty Niche and Develop into Functional Tissue-Resident Macrophages. *Immunity* 44:755-768.

Walkley, S. U., M. A. Thrall, K. Dobrenis, M. Huang, P. A. March, D. A. Siegel, and S. Wurzelmann. 1994. Bone marrow transplantation corrects the enzyme defect in neurons of the central nervous system in a lysosomal storage disease. *Proceedings of the National Academy of Sciences of the United States of America* 91:2970-2974.

Wang, Y., T. K. Ulland, J. D. Ulrich, W. Song, J. A. Tzaferis, J. T. Hole, P. Yuan, T. E. Mahan, Y. Shi, S. Gilfillan, M. Cella, J. Grutzendler, R. B. DeMattos, J. R. Cirrito, D. M. Holtzman, and M. Colonna. 2016. TREM2-mediated early microglial response limits diffusion and toxicity of amyloid plaques. *The Journal of experimental medicine* 213:667-675.

Wu, D., and G. K. Smyth. 2012. Camera: a competitive gene set test accounting for inter-gene correlation. *Nucleic acids research* 40:e133.

Yamasaki, R., H. Lu, O. Butovsky, N. Ohno, A. M. Rietsch, R. Cialic, P. M. Wu, C. E. Doykan, J. Lin, A. C. Cotleur, G. Kidd, M. M. Zorlu, N. Sun, W. Hu, L. Liu, J. C. Lee, S. E. Taylor, L. Uehlein, D. Dixon, J. Gu, C. M. Floruta, M. Zhu, I. F. Charo, H. L. Weiner, and R. M. Ransohoff. 2014. Differential roles of microglia and monocytes in the inflamed central nervous system. *The Journal of experimental medicine* 211:1533-1549.

Yona, S., K. W. Kim, Y. Wolf, A. Mildner, D. Varol, M. Breker, D. Strauss-Ayali, S. Viukov, M. Guilliams, A. Misharin, D. A. Hume, H. Perlman, B. Malissen, E. Zelzer, and S. Jung. 2013. Fate mapping reveals origins and dynamics of monocytes and tissue macrophages under homeostasis. *Immunity* 38:79-91.

We claim:

1. A method of enhancing engraftment of hematopoietic-derived macrophages in the brain of a subject undergoing hematopoietic cell (HC) transplantation comprising administering to the subject a therapeutically effective amount of a microglia depleting agent, wherein the microglia depleting agent is a colony stimulating factor 1 receptor (CSF1R) antagonist.

2. The method of claim 1 wherein the microglia depleting agent is administered prior to the HCs.

3. The method of claim 1 wherein the microglia depleting agent is administered concurrently with the HCs.

4. The method of claim 1 wherein the microglia depleting agent is administered after the administration of the HCs.

5. The method of claim 1 wherein the CSF1R antagonist comprises PLX3397.

6. The method of claim 1 wherein the CSF1R antagonist comprises PLX5622.

7. The method of claim 1 wherein the engrafted cells do not alter brain function.

8. The method of claim 1 wherein the subject suffers from a leukodystrophy or from a disease mediated by microglial dysfunction.

9. The method of claim 8 wherein the disease mediated by microglial dysfunction is selected from the group consisting of Rett syndrome, Autism spectrum disorder, Alzheimer's disease, frontotemporal dementia, amyotrophic lateral sclerosis, adult-onset leukoencephalopathy with axonal spheroids and pigmented glia, and other disorders where replacing central nervous system (CNS) macrophages with donor cells would be beneficial.

* * * * *